United States Patent
Takagi et al.

(10) Patent No.: US 10,136,875 B2
(45) Date of Patent: Nov. 27, 2018

(54) ULTRASONIC DIAGNOSTIC APPARATUS AND ULTRASONIC DIAGNOSTIC METHOD

(71) Applicant: Konica Minolta Inc., Tokyo (JP)

(72) Inventors: Kazuya Takagi, Toyonaka (JP); Satoshi Kondo, Yawata (JP); Mutsumi Nishida, Sapporo (JP)

(73) Assignee: Konica Minolta, Inc., Tokyo (JP)

( * ) Notice: Subject to any disclaimer, the term of this patent is extended or adjusted under 35 U.S.C. 154(b) by 748 days.

(21) Appl. No.: 14/435,023

(22) PCT Filed: Oct. 11, 2013

(86) PCT No.: PCT/JP2013/006113
§ 371 (c)(1),
(2) Date: Apr. 10, 2015

(87) PCT Pub. No.: WO2014/061258
PCT Pub. Date: Apr. 24, 2014

(65) Prior Publication Data
US 2015/0297172 A1   Oct. 22, 2015

(30) Foreign Application Priority Data
Oct. 19, 2012   (JP) ................... 2012-232041

(51) Int. Cl.
*A61B 8/08*   (2006.01)
*A61B 8/00*   (2006.01)
(Continued)

(52) U.S. Cl.
CPC .............. *A61B 8/08* (2013.01); *A61B 8/06* (2013.01); *A61B 8/085* (2013.01); *A61B 8/461* (2013.01);
(Continued)

(58) Field of Classification Search
CPC ......... A61B 8/085; A61B 8/06; A61B 8/5223; A61B 8/4461; A61B 8/461; A61B 8/08;
(Continued)

(56) References Cited

U.S. PATENT DOCUMENTS 5,577,505 A   11/1996   Brock-Fisher et al.
5,632,277 A   5/1997   Chapman et al.
(Continued)

FOREIGN PATENT DOCUMENTS

JP   2010005263 A   1/2010
JP   2010158360 A   7/2010

OTHER PUBLICATIONS

Masahisa Abe, et al; Kan saibo gan to ten'isei kangan no hen'en echo no hikaku; Journal of Medical Ultrasonics; Apr. 2010; vol. 37, No. 2; pp. 157-166 (no English translation provided).
(Continued)

*Primary Examiner* — Bo Joseph Peng
(74) *Attorney, Agent, or Firm* — Lucas & Mercanti, LLP

(57) ABSTRACT

An ultrasonic diagnostic apparatus (100) that decides a type of a tumor contained in a specimen includes: an image forming unit (103) that forms an ultrasonic image corresponding to an echo signal received from the specimen after administration of a contrast medium; a feature value calculating unit (106) that classifies each of a plurality of pixel regions contained in a tumor region including the tumor in the ultrasonic image into a low-luminance region, or a high-luminance region having higher luminance than the luminance of the low-luminance region, and calculates, based on a difference between a variance at a position of the low-luminance region and a variance at a position of the high-luminance region, a ring level indicating a degree of a ring shape of an image of the tumor region, the ring shape in which a luminance value of a central portion is lower than
(Continued)

a luminance value of a peripheral portion surrounding the central portion; and a type deciding unit (107) that decides the type of the tumor based on the ring level.

7 Claims, 23 Drawing Sheets

(51) Int. Cl.
    *G06K 9/46*     (2006.01)
    *G06T 7/00*     (2017.01)
    *A61B 8/06*     (2006.01)
    *G06K 9/52*     (2006.01)

(52) U.S. Cl.
    CPC .............. *A61B 8/463* (2013.01); *A61B 8/481* (2013.01); *A61B 8/5223* (2013.01); *G06K 9/4647* (2013.01); *G06K 9/4661* (2013.01); *G06K 9/4671* (2013.01); *G06K 9/52* (2013.01); *G06T 7/0012* (2013.01); *A61B 8/4461* (2013.01); *G06K 2209/051* (2013.01); *G06K 2209/053* (2013.01); *G06T 2207/10132* (2013.01); *G06T 2207/30096* (2013.01)

(58) Field of Classification Search
    CPC ...... A61B 8/463; A61B 8/481; G06K 9/4647; G06K 9/52; G06K 9/4671; G06K 9/4661; G06K 2209/051; G06K 2209/053; G06T 7/0012; G06T 2207/10132; G06T 2207/30096

See application file for complete search history.

(56) References Cited

U.S. PATENT DOCUMENTS

| | | | |
|---|---|---|---|
| 5,706,819 A | 1/1998 | Hwang et al. | |
| 7,099,502 B2 * | 8/2006 | Shams ..................... | G06K 9/00 382/129 |
| 2004/0151383 A1 * | 8/2004 | Alessi ..................... | G06K 9/00 382/224 |
| 2008/0247651 A1 * | 10/2008 | Takaki ................ | G06K 9/4671 382/219 |
| 2008/0279441 A1 * | 11/2008 | Matsuo .............. | G01N 15/1475 382/133 |
| 2011/0103698 A1 * | 5/2011 | Hayashi ............... | G06K 9/4652 382/201 |
| 2012/0070049 A1 * | 3/2012 | Iwase .................... | G06T 7/0012 382/128 |
| 2015/0003706 A1 * | 1/2015 | Eftestol ................ | G06T 7/0012 382/131 |

OTHER PUBLICATIONS

International Search Report dated Nov. 5, 2013 for PCT/JP2013/006113.

* cited by examiner

FIG. 1

| | | VASCULAR PHASE | | POST VASCULAR PHASE |
|---|---|---|---|---|
| | | ARTERY PHASE | PORTAL PHASE | |
| MALIGNANT | HEPATOMA | hyper | iso | hypo |
| | METASTATIC LIVER CANCER | ring / hyper | hypo | hypo |
| BENIGN | HEMANGIOMA OF LIVER | ring→ | ring→ | hypo |
| | FNH | center→ | iso | iso | hyper  HYPERECHOGENIC WITH RESPECT TO SURROUNDINGS
iso    ISOECHOGENIC WITH RESPECT TO SURROUNDINGS
hypo   HYPOECHOGENIC WITH RESPECT TO SURROUNDINGS
ring   RING PATTERN
center CENTER PATTERN

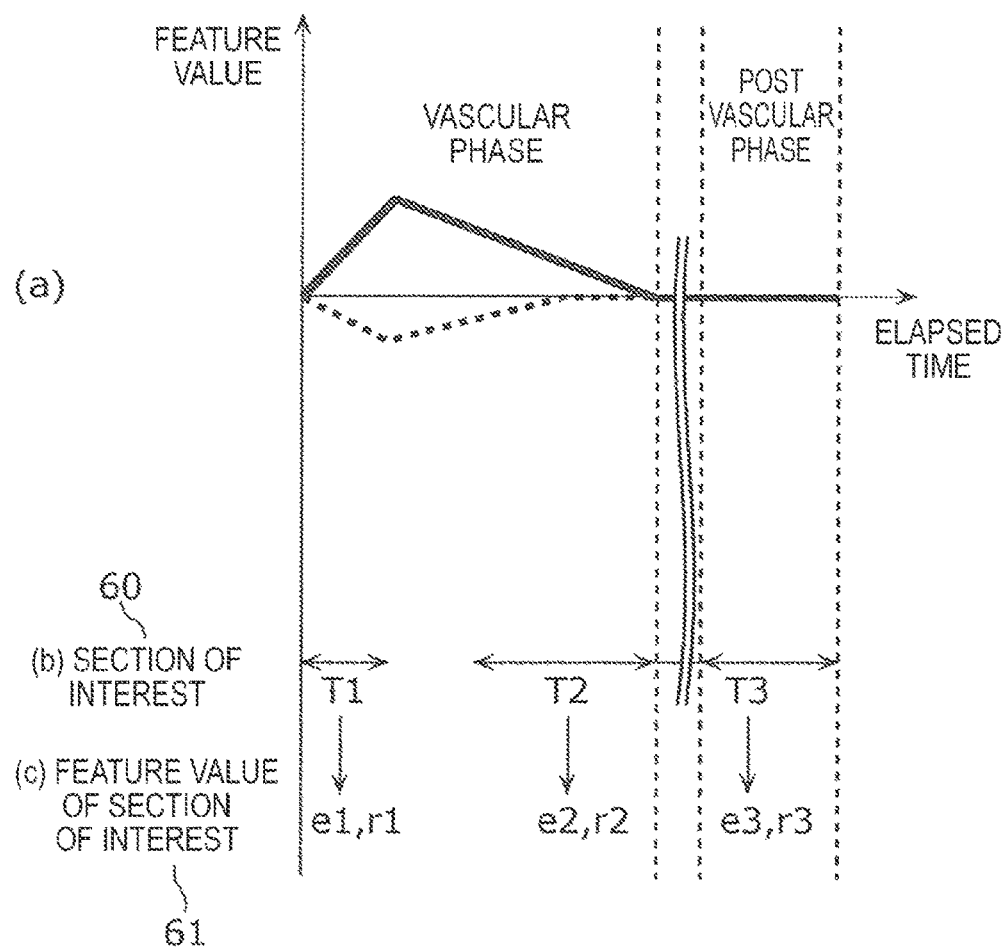

ULTRASONIC DIAGNOSTIC APPARATUS AND ULTRASONIC DIAGNOSTIC METHOD

CROSS REFERENCE TO RELATED APPLICATION

This Application is a 371 of PCT/JP2013/006113 filed on Oct. 11, 2013 which, in turn, claimed the priority of Japanese Patent Application No. JP2012-232041 filed on Oct. 19, 2012, both applications are incorporated herein by reference.

TECHNICAL FIELD

The present invention relates to an ultrasonic diagnostic apparatus and an ultrasonic diagnostic method. More particularly, the present invention relates to an ultrasonic diagnostic apparatus and an ultrasonic diagnostic method for deciding a type of a tumor contained in a specimen.

BACKGROUND ART

Ultrasonography is one of image diagnostic methods capable of forming highly sensitive images of blood vessels by administration of a contrast medium into the blood vessels. In Japan, the use of a contrast medium called Sonazoid is currently approved for diagnosing liver tumors and mammary tumors. The contrast medium of Sonazoid is employed for deciding types of tumors.

In practical situations of diagnosis, an operator initially checks the presence or absence of a tumor. A tumor is recognized as a hypoechogenic region or a hyperechogenic region in an ultrasonic image. Then, a contrast medium is administrated, and the tumor is imaged.

At present, a tumor type decision is made based on subjective decision of a person reading images (operator). This situation causes a problem that diagnosis results are dependent on the person reading the images.

For overcoming this problem, Patent Literature 1 discloses objective differential diagnostic methods based on time-series changes of two types of feature values, i.e., average luminance and standard deviations exhibited in a tumor region.

According to the technology disclosed in Patent Literature 1, large and small three circles containing a tumor are defined, and comparisons are made between temporal waveforms of the feature values in the respective circles and typical waveforms of respective types. Then, the type producing the closest waveforms is decided as the type of the tumor. Alternatively, the type producing feature values closest to the feature values of the three circles is decided for each time phase. Then, the type decided the largest number of times is decided as the type of the tumor.

CITATION LIST

Patent Literatures

Patent Literature 1: JP 2010-005263 A
Patent Literature 2: U.S. Pat. No. 5,632,277
Patent Literature 3: U.S. Pat. No. 5,706,819
Patent Literature 4: U.S. Pat. No. 5,577,505

Non Patent Literature

Non Patent Literature 1: Ultrasonic Diagnostic Criteria for Liver Tumor (Proposal) http://www.jsum.or.jp/committee/diagnostic/pdf/liver_tumor.pdf

SUMMARY OF INVENTION

Technical Problem

According to the foregoing tumor type decision methods, however, highly accurate tumor type decision has been demanded.

Accordingly, it is an object of the present invention to provide an ultrasonic diagnostic apparatus capable of deciding tumor types with high accuracy.

Solution to Problem

In order to achieve the above object, an ultrasonic diagnostic apparatus according to an aspect of the present invention is an ultrasonic diagnostic apparatus that decides a type of a tumor contained in a specimen, and includes: an image forming unit that forms an ultrasonic image corresponding to an echo signal received from the specimen after administration of a contrast medium; a feature value calculating unit that classifies each of a plurality of pixel regions contained in a tumor region including the tumor in the ultrasonic image into a low-luminance region, or a high-luminance region having higher luminance than the luminance of the low-luminance region, and calculates, based on a difference between a variance at a position of the low-luminance region and a variance at a position of the high-luminance region, a ring level indicating a degree of a ring shape of an image of the tumor region, the ring shape in which a luminance value of a central portion is lower than a luminance value of a peripheral portion surrounding the central portion; and a type deciding unit that decides the type of the tumor based on the ring level.

The foregoing general or specific aspects may be realized in the form of a system, a method, an integrated circuit, a computer program, or a recording medium such as a CD-ROM readable by a computer, or may be realized by arbitrary combinations of a system, a method, an integrated circuit, a computer program, and a recording medium.

Advantageous Effects of Invention

According to the present invention, there can be provided an ultrasonic diagnostic apparatus capable of deciding tumor types with high accuracy.

BRIEF DESCRIPTION OF DRAWINGS

FIG. 1 is a view illustrating imaging patterns of a liver tumor.

FIG. 9 is a view illustrating a tumor type deciding process based on the feature values according to the first embodiment.

FIG. 10 is a view illustrating a further example of the display screen according to the first embodiment.

DESCRIPTION OF EMBODIMENTS

Findings on which the Present Invention is Based

The present inventors have found that the following problems arise from the type decision methods described in the section of "Background Art".

FIG. 1 illustrates a typical example of imaging patterns of a liver tumor (Non Patent Literature 1).

There are roughly two types of imaging time phases. One type of the imaging time phases is a vascular phase as a time phase after an elapse of approximately two minutes from administration of a contrast medium, while the other is a post vascular phase as a time phase after an elapse of approximately ten minutes and longer. The vascular phase is a time phase when a time-series change is remarkable in an imaging pattern, while the post vascular phase is a time phase when a time-series change is small in an imaging pattern. In more detail, the vascular phase is divided into an artery phase where predominant entrance of blood is from an artery which supplies oxygen to the liver, and a portal phase where predominant entrance of blood is from a portal. With a rise of malignancy of a tumor, it is considered that the supply of oxygen from the artery becomes more predominant along with decrease in the entrance of blood from the portal.

In practical situations of diagnosis, a user observes time-series changes of these imaging patterns to decide a tumor type. For example, hepatoma is suspected in case of indications of hyperechogenic for a tumor region in comparison with a parenchyma region in the vascular phase, and hypoechogenic for the tumor region in comparison with the parenchyma region in the post vascular phase.

Under the present circumstances, a tumor type decision is made based on subjective decision of a person reading images (user). In this case, such a problem arises that diagnosis results are dependent on the person reading images.

As illustrated in FIG. 1, useful information for making decision in practical differentiations includes a difference between a tumor region and a parenchyma region, and imaging patterns in a tumor region (such as ring pattern, center pattern, and iso-pattern).

According to the first method of Patent Literature 1, imaging patterns are decided based on standard deviations. In this case, however, it may occur that the standard deviation of the center pattern becomes equivalent to the standard deviation of the ring pattern, in which condition accurate decision may be difficult to make.

Figure 2:
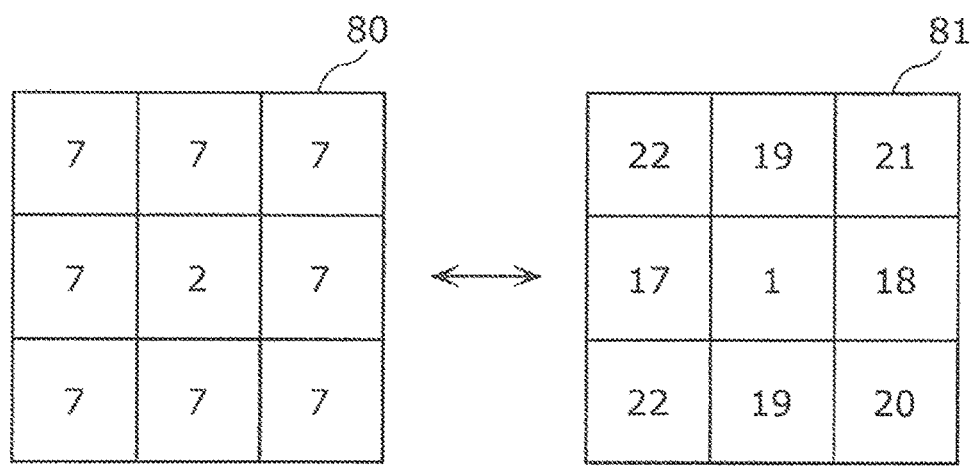
FIG. 2 is a view illustrating a problem.

On the other hand, the second method of Patent Literature 1 evaluates spatial patterns in three circles to evaluate a pattern in a tumor region. According to this method, however, the pattern in the tumor region is determined based on a deviation between a predetermined pattern and the pattern in the tumor region corresponding to the decision target. In this case, discrepancy between an input pattern 81 and a predetermined pattern 80 increases when the input pattern 81 exhibits a high-degree ring pattern as illustrated in FIG. 2, for example. In this condition, the degree of the pattern may be difficult to accurately evaluate.

Moreover, there is a possibility of disagreement between the center of a ring pattern and the center of the tumor region. In this case, the degree of the ring pattern may be similarly difficult to accurately evaluate.

An ultrasonic diagnostic apparatus according to an aspect of the present invention is an ultrasonic diagnostic apparatus that decides a type of a tumor contained in a specimen, and includes: an image forming unit that forms an ultrasonic image corresponding to an echo signal received from the specimen after administration of a contrast medium; a feature value calculating unit that classifies each of a plurality of pixel regions contained in a tumor region including the tumor in the ultrasonic image into a low-luminance region, or a high-luminance region having higher luminance than the luminance of the low-luminance region, and calculates, based on a difference between a variance at a position of the low-luminance region and a variance at a position of the high-luminance region, a ring level indicating a degree of a ring shape of an image of the tumor region, the ring shape in which a luminance value of a central portion is lower than a luminance value of a peripheral portion surrounding the central portion; and a type deciding unit that decides the type of the tumor based on the ring level.

The ultrasonic diagnostic apparatus thus constructed can decide the degree of the ring pattern based on the variance of the high-luminance region and the variance of the low-luminance region. In this case, the ultrasonic diagnostic apparatus can decide the degree of the ring pattern with high accuracy even when the center of the ring pattern is not present at the center of the tumor region, for example. Accordingly, the ultrasonic diagnostic apparatus can decide the type of the tumor with high accuracy.

For example, the feature value calculating unit may set the ring level to a second value when a difference value obtained by subtracting the variance at the position of the low-luminance region from the variance at the position of the high-luminance region is a first value, and set the ring level to a fourth value larger than the second value when the difference value is a third value larger than the first value.

For example, the feature value calculating unit may classify each of the regions into the low-luminance region when the luminance value of the region is smaller than a predetermined threshold, and classify each of the regions into the high-luminance region when the luminance value of the region is larger than the threshold.

For example, the feature value calculating unit may calculate a number sequence indicating a time-series change of the luminance value for each of the regions, classify each of the regions into the low-luminance region when a difference between the maximum luminance value and the minimum luminance value in the number sequence is smaller than a predetermined threshold, and classify each of the pixels into the high-luminance region when the difference in the number sequence is larger than the threshold.

For example, the feature value calculating unit may further calculate a difference between luminance of a parenchyma region contained in the ultrasonic image and not including the tumor, and luminance of the tumor region, and the type deciding unit may decide the type of the tumor based on the difference between the luminance of the parenchyma region and the luminance of the tumor region, and on the ring level.

The ultrasonic diagnostic apparatus thus constructed can decide the type of the tumor based on the luminance difference between the tumor region and the parenchyma region in the ultrasonic image as well as the ring level. Accordingly, the ultrasonic diagnostic apparatus can decide the type of the tumor with higher accuracy.

An ultrasonic diagnostic method according to an aspect of the present invention is an ultrasonic diagnostic method that decides a type of a tumor contained in a specimen, and includes: an image forming step that forms an ultrasonic image corresponding to an echo signal received from the specimen after administration of a contrast medium; a feature value calculating step that classifies each of a plurality of pixel regions contained in a tumor region including the tumor in the ultrasonic image into a low-luminance region, or a high-luminance region having higher luminance than the luminance of the low-luminance region, and calculates, based on a difference between a variance at a position of the low-luminance region and a variance at a position of the high-luminance region, a ring level indicating a degree of a ring shape of an image of the tumor region, the ring shape in which a luminance value of a central portion is lower than a luminance value of a peripheral portion surrounding the central portion; and a type deciding step that decides the type of the tumor based on the ring level.

The ultrasonic diagnostic method having this configuration can decide the degree of the ring pattern based on the variance of the high-luminance region and the variance of the low-luminance region. In this case, the ultrasonic diagnostic method can decide the degree of the ring pattern with high accuracy even when the center of the ring pattern is not present at the center of the tumor region, for example. Accordingly, the ultrasonic diagnostic method can decide the type of the tumor with high accuracy.

An ultrasonic diagnostic apparatus according to an aspect of the present invention is an ultrasonic diagnostic apparatus that decides a type of a tumor contained in a specimen, and includes: an image forming unit that forms an ultrasonic image corresponding to an echo signal received from the specimen after administration of a contrast medium into the specimen; a region of interest setting unit that searches for a first region of interest corresponding to a central portion in a ring shape in a tumor region containing the tumor in the ultrasonic image, the ring shape in which a luminance value of the central portion is lower than a luminance value of a peripheral portion surrounding the central portion; a feature value calculating unit that calculates a difference between luminance of the first region of interest and luminance of a second region of interest corresponding to the peripheral portion to designate the difference as a ring level indicating a degree of the ring shape of an image of the tumor region; and a type deciding unit that decides the type of the tumor based on the ring level.

The ultrasonic diagnostic apparatus thus constructed can decide the degree of the ring pattern with high accuracy based on the search for the low-luminance region within the tumor region even when the center of the ring pattern is not present at the center of the tumor region, for example. Accordingly, the ultrasonic diagnostic apparatus can decide the type of the tumor with high accuracy.

For example, in a plurality of search regions in a predetermined size contained in the tumor region and located at different positions, the region of interest setting unit may search for the search region where a luminance difference between a first region in a range determined beforehand in the search regions and a second region in a range determined beforehand and surrounding the first region becomes the maximum, and may set the first region contained in the search region where the luminance difference becomes the maximum as the first region of interest.

The ultrasonic diagnostic apparatus thus constructed can appropriately set the first region of interest corresponding to the central portion of the ring pattern within the tumor region. Accordingly, the ultrasonic diagnostic apparatus can decide the type of the tumor with high accuracy.

For example, for the region of interest setting unit, the first region may be substantially circular, and the second region may be a substantially circular region centered at the center of the first region and corresponding a portion other than the first region.

The ultrasonic diagnostic apparatus thus constructed can set the first region of interest regardless of the position or shape of the central portion of the tumor region. Accordingly, the ultrasonic diagnostic apparatus can decide the type of a liver tumor with high accuracy.

For example, the image forming unit may form ultrasonic images in a plurality of time phases including an artery phase, the region of interest setting unit may set the first region of interest in the ultrasonic image in the artery phase, and the feature value calculating unit may calculate the plurality of ring levels in the plurality of time phases based on the set first region of interest, and the type deciding unit may decide the type of the tumor based on the plurality of calculated ring levels.

The ultrasonic diagnostic apparatus thus constructed can prevent shift of the position of the first region of interest for each time phase. Accordingly, the ultrasonic diagnostic apparatus can decide the tumor type with high accuracy.

For example, in a plurality of search regions in a predetermined size contained in the tumor region and located at different positions, the region of interest setting unit may search for the search region exhibiting the minimum luminance, and may set the search region exhibiting the minimum luminance as the first region of interest.

The ultrasonic diagnostic apparatus thus constructed can appropriately set the first region of interest corresponding to the central portion of the ring pattern within the tumor region. Accordingly, the ultrasonic diagnostic apparatus can decide the type of the tumor with high accuracy.

An ultrasonic diagnostic method according to an aspect of the present invention is an ultrasonic diagnostic method that decides a type of a tumor contained in a specimen, and includes: an image forming step that forms an ultrasonic image corresponding to an echo signal received from the specimen after administration of a contrast medium; a region of interest setting step that searches for a first region of interest corresponding to a central portion in a ring shape in a tumor region containing the tumor in the ultrasonic image, the ring shape in which a luminance value of the central portion is lower than a luminance value of a peripheral portion surrounding the central portion; a feature value calculating step that calculates a difference between luminance of the first region of interest and luminance of a second region of interest corresponding to the peripheral portion to designate the difference as a ring level indicating a degree of the ring shape of an image of the tumor region; and a type deciding step that decides the type of the tumor based on the ring level.

The ultrasonic diagnostic method having this configuration can decide the degree of the ring pattern with high accuracy based on the search for the low-luminance region within the tumor region even when the center of the ring pattern is not present at the center of the tumor region, for example. Accordingly, the ultrasonic diagnostic method can decide the type of the tumor with high accuracy.

An ultrasonic diagnostic apparatus according to an aspect of the present invention is an ultrasonic diagnostic apparatus that decides a type of a tumor contained in a specimen, and includes: an image forming unit that forms an ultrasonic image corresponding to an echo signal received from the specimen after administration of a contrast medium; a feature value calculating unit that projects luminance values of a plurality of pixels contained in a tumor region including the tumor in the ultrasonic image such that the luminance values are projected in a horizontal direction and a vertical direction, and calculates, based on degrees of downward convexity exhibited in the projected results, a ring level indicating a degree of a ring shape of an image of the tumor region, the ring shape in which a luminance value of the central portion is lower than a luminance value of a peripheral portion surrounding the central portion, the ring level calculated; and a type deciding unit that decides the type of the tumor based on the ring level.

The ultrasonic diagnostic apparatus thus constructed calculates the degree of the ring pattern based on the projected results of the luminance values within the tumor region as projected in the horizontal direction and the vertical direction. In this case, the ultrasonic diagnostic apparatus can decide the degree of the ring pattern with high accuracy even when the center of the ring pattern is not present at the center of the tumor region, for example. Accordingly, the ultrasonic diagnostic apparatus can decide the type of the tumor with high accuracy.

An ultrasonic diagnostic method according to an aspect of the present invention is an ultrasonic diagnostic method that decides a type of a tumor contained in a specimen, and includes: an image forming step that forms an ultrasonic image corresponding to an echo signal received from the specimen after administration of a contrast medium; a feature value calculating step that projects luminance values of a plurality of pixels contained in a tumor region including the tumor in the ultrasonic image such that the luminance values are projected in a horizontal direction and a vertical direction, and calculates, based on degrees of downward convexity exhibited in the projected results, a ring level indicating a degree of a ring shape of an image of the tumor region, the ring shape in which a luminance value of the central portion is lower than a luminance value of a peripheral portion surrounding the central portion, the ring level calculated; and a type deciding step that decides the type of the tumor based on the ring level.

The ultrasonic diagnostic method having this configuration calculates the degree of the ring pattern based on the projected results of the luminance values within the tumor region as projected in the horizontal direction and the vertical direction. In this case, the ultrasonic diagnostic method can decide the degree of the ring pattern with high accuracy even when the center of the ring pattern is not present at the center of the tumor region, for example. Accordingly, the ultrasonic diagnostic method can decide the type of the tumor with high accuracy.

The foregoing general or specific aspects may be realized in the form of a system, a method, an integrated circuit, a computer program, or a recording medium such as a CD-ROM readable by a computer, or may be realized by arbitrary combinations of a system, a method, an integrated circuit, a computer program, and a recording medium.

An ultrasonic diagnostic apparatus according to an aspect of the present invention is hereinafter described with reference to the drawings.

Each of embodiments discussed hereinbelow illustrates a preferable specific example of the present invention. Numerical values, shapes, materials, constituent elements, the positions and connection forms of the constituent elements, steps, the order of the steps, and others are presented by way of example only, and not intended to limit the present invention. In addition, constituent elements not included in the independent claims defining the uppermost concepts of the present invention are presented as arbitrary constituent elements included in more preferable modes.

Configuration and operation of a system are now described.

First Embodiment

Discussed in this embodiment is an example which adopts feature values reflecting a luminance difference between a tumor region (target region) and a parenchyma region in an ultrasonic image, and imaging patterns (such as ring pattern, center pattern, and iso-pattern) in the tumor region to decide a type of a liver tumor with high accuracy. The "tumor" in this context refers to a tissue exhibiting properties different from those of other tissues, including both a benign tumor and a malignant tumor.

Figure 3:
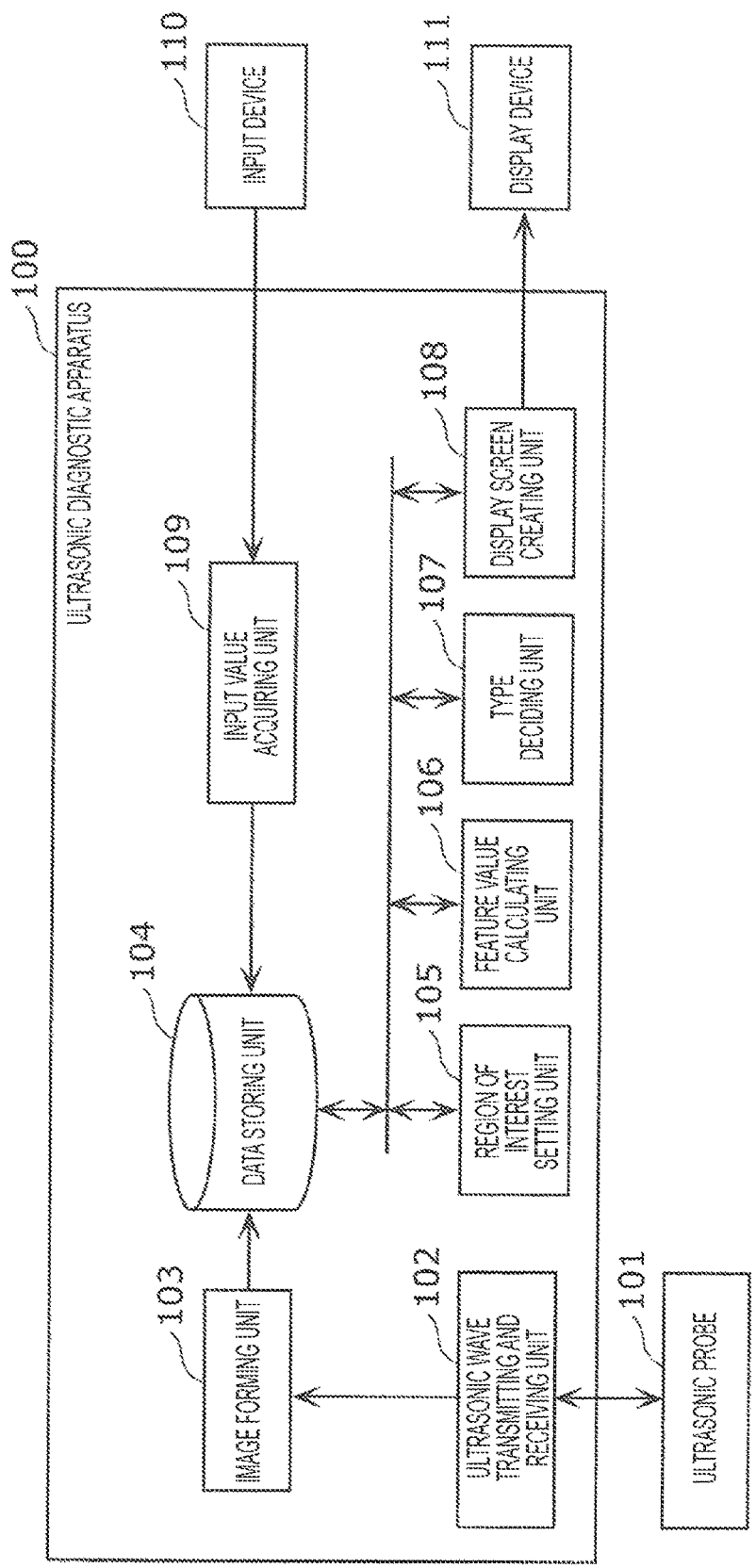
FIG. 3 is a block diagram illustrating a configuration of an ultrasonic diagnostic apparatus according to a first embodiment.

FIG. 3 is a block diagram illustrating a configuration of an ultrasonic diagnostic apparatus 100 according to this embodiment.

As illustrated in FIG. 3, an ultrasonic system according to this embodiment includes the ultrasonic diagnostic apparatus 100, an ultrasonic probe 101, an input device 110, and a display device 111. The ultrasonic diagnostic apparatus 100 includes an ultrasonic wave transmitting and receiving unit 102, an image forming unit 103, a data storing unit 104, a region of interest setting unit 105, a feature value calculating unit 106, a type deciding unit 107, a display screen creating unit 108, and an input value acquiring unit 109.

(Configuration)

The ultrasonic probe 101 converts electric signals output from the ultrasonic wave transmitting and receiving unit 102 into ultrasonic waves, and transmits the ultrasonic waves to a specimen. Then, the ultrasonic probe 101 receives echo signals reflected on the specimen and returning to the ultrasonic probe 101, converts the received echo signals into electric signals, and outputs the electric signals to the ultrasonic wave transmitting and receiving unit 102.

The ultrasonic wave transmitting and receiving unit 102 generates electric signals corresponding to original signals of ultrasonic signals, and outputs the generated electric signals to the ultrasonic probe 101. In addition, the ultrasonic wave transmitting and receiving unit 102 converts electric signals output from the ultrasonic probe 101 into digital echo signals, and outputs the echo signals to the image forming unit 103.

The image forming unit 103 converts the echo signals output from the ultrasonic wave transmitting and receiving unit 102 into luminance values to form an ultrasonic image. The image forming unit 103 stores the formed ultrasonic image in the data storing unit 104.

The data storing unit 104 stores the input image (ultrasonic image), information on a cross section of interest including a tumor, information on regions of interest used for type decision, learning data used for type decision, feature values of input data used for type decision, and others.

The input value acquiring unit 109 acquires information on the cross section of interest, the regions of interest and others designated by an operator via the input device 110, and stores this information in the data storing unit 104.

The region of interest setting unit 105 reads an image of the cross section of interest and the input image from the data storing unit 104, and calculates a positional deviation between these images. Then, the region of interest setting unit 105 reads information on the regions of interest from the data storing unit 104, and corrects the positions of the regions of interest in the input image based on the calculated positional deviation. Thereafter, the region of interest setting unit 105 stores the corrected information on the regions of interest in the data storing unit 104.

The feature value calculating unit 106 reads the input image and the corrected information on the regions of interest from the data storing unit 104, and extracts predetermined feature values from the regions of interest in the input image. Then, the feature value calculating unit 106 arranges the calculated feature values in time series, and stores the feature values in the data storing unit 104.

The type deciding unit 107 reads, from the data storing unit 104, feature values in the range from administration of a contrast medium to a post vascular phase, and learning data for each type, and then decides the tumor type based on the obtained information. The type deciding unit 107 having decided the tumor type stores the type decision result in the data storing unit 104.

The display screen creating unit 108 reads the input image, the feature values, the type decision result and others from the data storing unit 104 to create a display screen based on the obtained information. The display screen thus created is displayed on the display device 111.

The input device 110 receives input from the operator. The input device 110 is constituted by a trackball, a button, a touch panel or the like.

The display device 111 displays the display screen created by the display screen creating unit 108. The display device 111 is constituted by a display or the like.

Discussed hereinabove is the apparatus configuration according to this embodiment.

(Operation)

The flow of operation according to this embodiment is hereinafter described.

Figure 4:
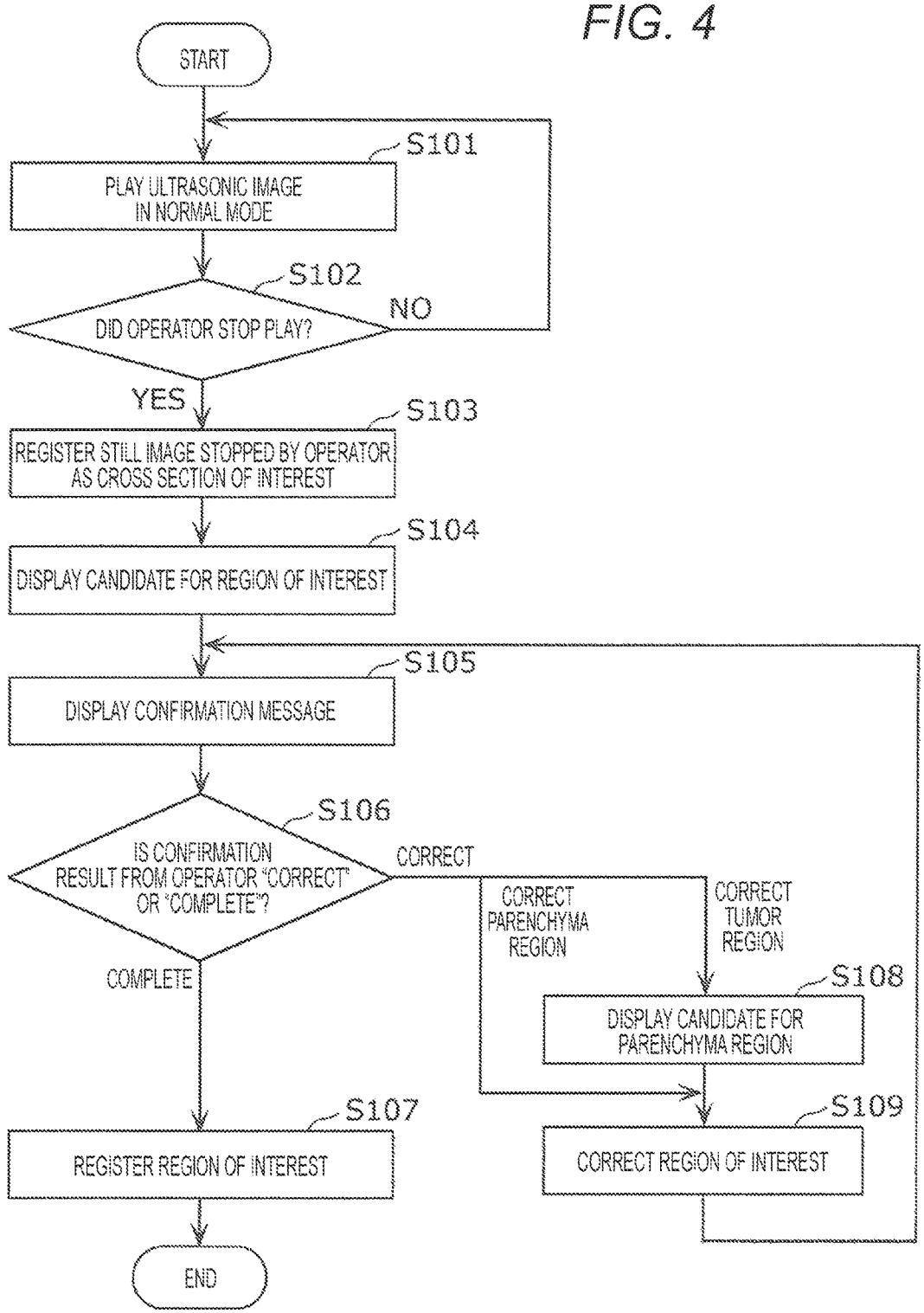
FIG. 4 is a flowchart showing operation executed by the ultrasonic diagnostic apparatus prior to administration of a contrast medium according to the first embodiment.

Operation executed by the ultrasonic diagnostic apparatus 100 prior to administration of a contrast medium is discussed at first. FIG. 4 is a flowchart showing operation prior to administration of the contrast medium according to this embodiment.

[Step S101]

Initially, the image forming unit 103 converts echo signals output from the ultrasonic wave transmitting and receiving unit 102 into luminance values to form an ultrasonic image. Then, the image forming unit 103 stores the ultrasonic image thus formed in the data storing unit 104 as an input image. The display screen creating unit 108 reads the input image from the data storing unit 104 where the input image has been stored by the image forming unit 103. Then, the display screen creating unit 108 integrates the input image with patient information, setting information and others to create a display screen, and displays the created display screen on the display device 111. A display mode for this display is referred to as a normal mode. The normal mode corresponds to a display mode prior to administration of the contrast medium.

[Step S102]

In step S101, the input value acquiring unit 109 receives operation of play stop from the operator. When the operator inputs operation for stopping play through the input device 110, the flow goes to step S103 to execute a process in step S103. On the other hand, when the operator does not input operation for stopping play, the flow returns to step S101.

[Step S103]

When it is detected that the operator has input play stop operation through the input device 110, the ultrasonic wave transmitting and receiving unit 102 and the image forming unit 103 stop transmission and reception of ultrasonic waves and image formation, respectively. Then, the display screen creating unit 108 displays a still image on the display device 111. The region of interest setting unit 105 registers an ultrasonic image stored in the data storing unit 104 and corresponding to an image in a stop state as a cross section of interest.

[Step S104]

When the operator inputs type decision operation through the input device 110 in a subsequent step, the region of interest setting unit 105 detects candidates for a tumor region and a parenchyma region, i.e., regions of interest, from the cross section of interest, and stores the detection results in the data storing unit 104 as information on the regions of interest. Then, the display screen creating unit 108 reads information on the cross section of interest and the regions of interest from the data storing unit 104 where the information has been stored by the region of interest setting unit 105, creates a display screen which contains the information indicating the regions of interest superimposed on the cross section of interest, and displays the created display screen on the display device 111. On the display screen, the outer edges of the regions of interest are displayed in broken lines, for example. Alternatively, the entire regions of interest are colored to such an extent that the image of the cross section of interest can be seen through the regions of interest.

Figure 5:
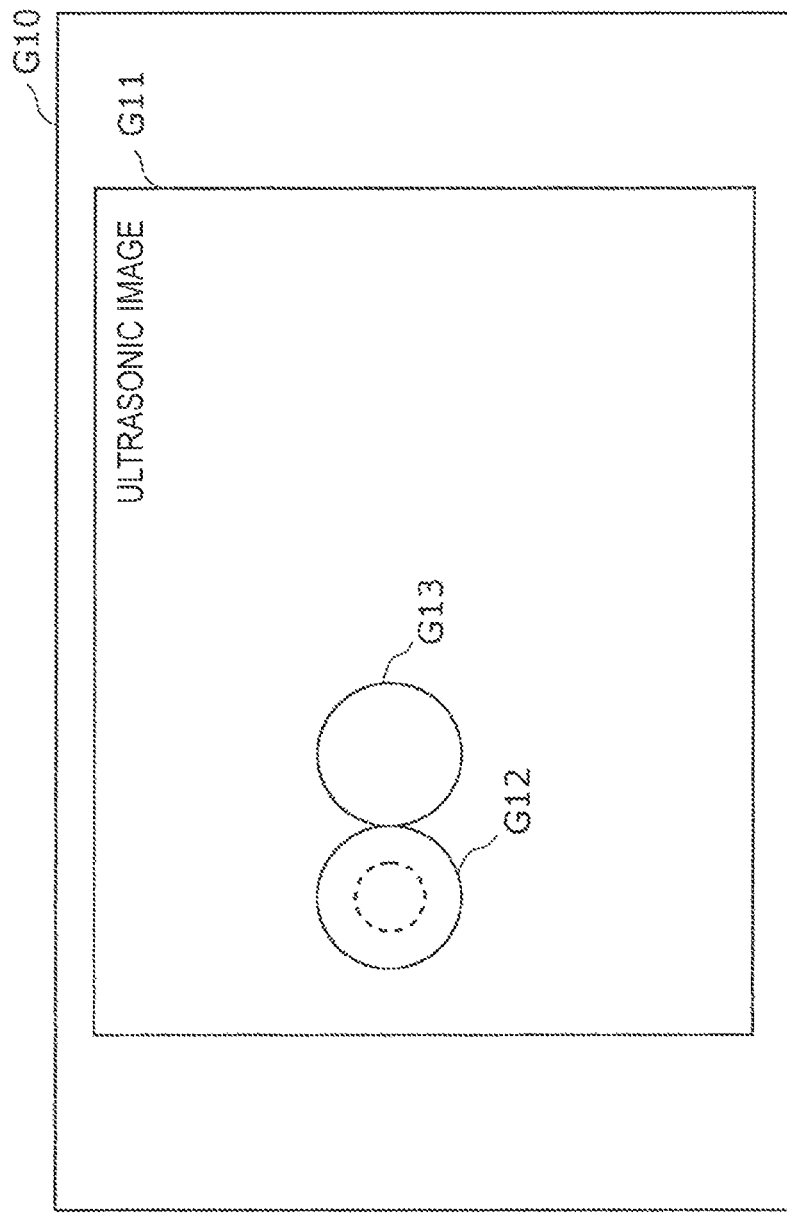
FIG. 5 is a view illustrating an example of a display screen according to the first embodiment.

FIG. 5 illustrates an example of the display screen in the normal mode. In FIG. 5, an ultrasonic image G11 is displayed on a display screen (normal mode) G10. The ultrasonic image G11 contains a tumor region G12 and a parenchyma region G13. The ultrasonic image G11 herein is an input image read from the data storing unit 104.

The region of interest setting unit 105 uses a two-dimensional differential filter to detect a candidate for the tumor region. The coefficients of the two-dimensional differential filter are so determined that a filter value becomes a large value in a region where the luminance distribution is low at the center and high in the periphery, and in a region where the luminance distribution is high at the center and low in the periphery. The region of interest setting unit 105 shifts the two-dimensional differential filter throughout the screen to calculate a filter value for each position.

A plurality of candidates in different sizes are detectable for the tumor region by varying the resolution of the input image corresponding to the filtering target. For example, when the resolution of the input image is changed to half of the resolution, a tumor in a size twice larger than the size of the tumor in the foregoing example is detectable by using the differential filter in the same size. Accordingly, a plurality of candidates in different sizes are detectable for the tumor region by the use of images in several patterns of resolution for detection of candidates for the tumor region.

The region of interest setting unit 105 having calculated filter values for the respective positions designates, as a candidate for the tumor region, the region having the maximum filter value in the plurality of calculated filter values.

In addition, the region of interest setting unit 105 designates, as a candidate for the parenchyma region, a region located at the same depth as the depth of the detected tumor region. The parenchyma region in this context refers to a normal region not containing a tumor. The parenchyma region is set to a region in the vicinity of the tumor region.

While the candidate for the tumor region is detected by using the two-dimensional differential filter according to the foregoing example, the tumor region may be determined based on reading of the ultrasonic image by the operator instead of the use of the differential filter.

Each shape of the tumor region and the parenchyma region is a circular or elliptical shape, for example, but is not limited to these shapes. The shapes of the tumor region and the parenchyma region may be arbitrary shapes such as a polygonal shape.

[Step S105]

Then, the display screen creating unit 108 displays, on the display device 111, a confirmation message for confirming whether or not the candidates for the regions of interest are appropriate.

[Step S106]

Then, the input value acquiring unit 109 receives input from the operator as a response to the confirmation message in step S105 via the input device 110. The input from the operator in response to the confirmation message is completion of setting of the regions of interest, or correction for the parenchyma region or the tumor region.

[Step S107]

When the operator inputs completion of setting of the regions of interest, the input value acquiring unit 109 makes a final decision on the information about the regions of interest stored in the data storing unit 104.

[Step S108]

When the operator corrects the tumor region through the input device 110 in response to the confirmation message in step S105, the region of interest setting unit 105 changes the parenchyma region in accordance with the correction of the tumor region. Then, the flow goes to step S109 to execute a process in step S109.

[Step S109]

When the operator corrects the parenchyma region through the input device 110 in response to the confirmation message in step S105, or after the parenchyma region is changed in step S108, the region of interest setting unit 105 corrects the information about the regions of interest stored in the data storing unit 104. Then, the flow returns to step S105, where the display screen creating unit 108 displays a confirmation message.

Discussed hereinabove is the flowchart showing settings of the cross section of interest, and regions of interest according to this embodiment.

Figure 6:
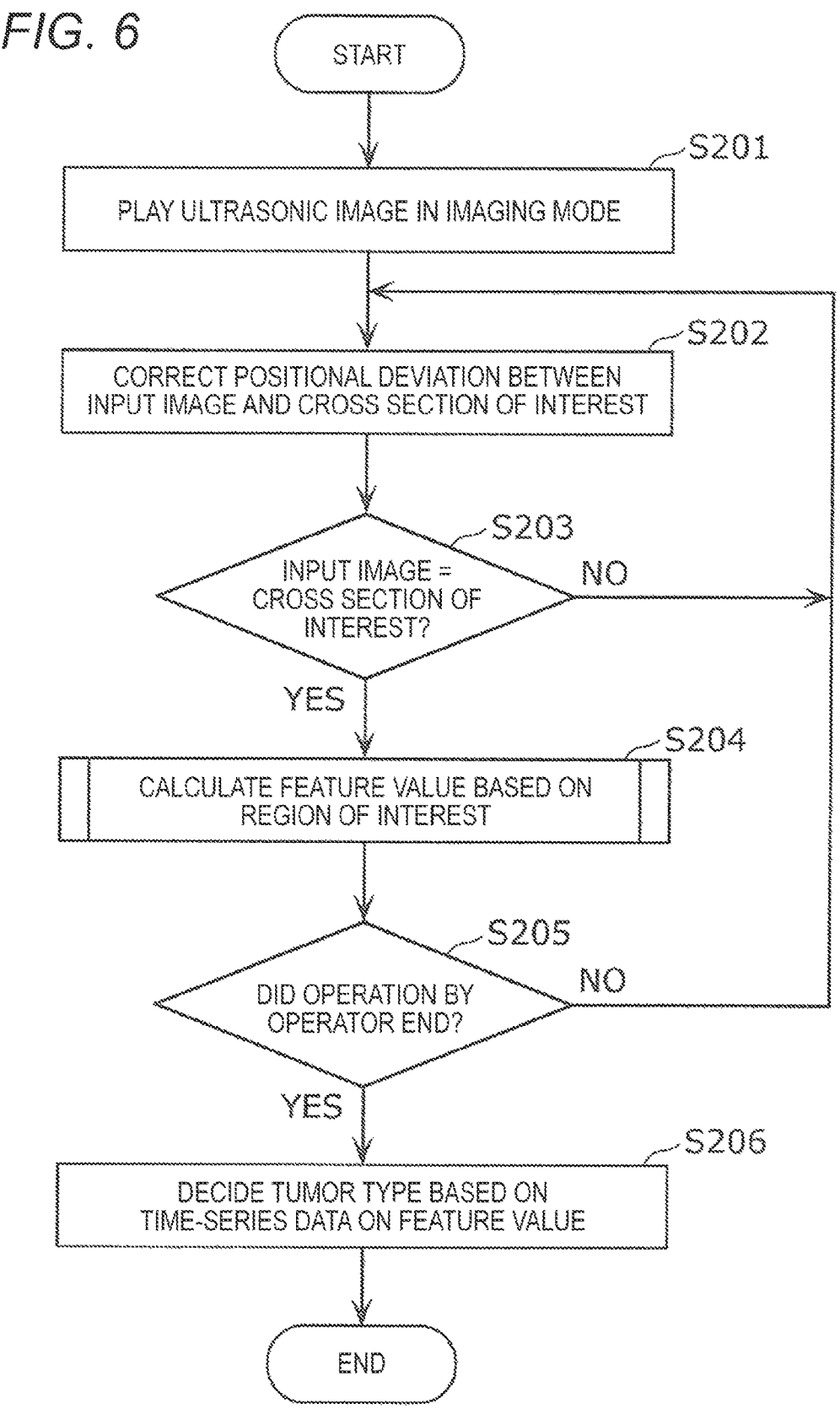
FIG. 6 is a flowchart showing operation executed by the ultrasonic diagnostic apparatus after administration of the contrast medium according to the first embodiment.

Operation executed by the ultrasonic diagnostic apparatus 100 after administration of the contrast medium is hereinafter described. FIG. 6 is a flowchart showing operation after administration of the contrast medium according to this embodiment.

[Step S201]

After the final decision is made on the regions of interest in the cross section of interest in step S107, the ultrasonic wave transmitting and receiving unit 102 and the image forming unit 103 initially execute transmission and reception of ultrasonic waves corresponding to imaging ultrasonic waves, and image formation, respectively. More specifically, the image forming unit 103 forms a contrast image G21 where reflection echo from the contrast medium is predominant, and a tissue image G22 where reflection echo from a tissue is predominant, by using known pulse inversion or amplitude modulation (see Patent Literatures 2, 3, and 4), for example. The tissue image G22 in this context is an image corresponding to fundamental wave components of received ultrasonic waves. Then, the image forming unit 103 stores the contrast image G21 and the tissue image G22 in the data storing unit 104. The display screen creating unit 108 reads the contrast image G21 and the tissue image G22 from the data storing unit 104 where the images have been stored by the image forming unit 103, and creates a display screen containing these images arranged in the left-right direction.

Figure 7:
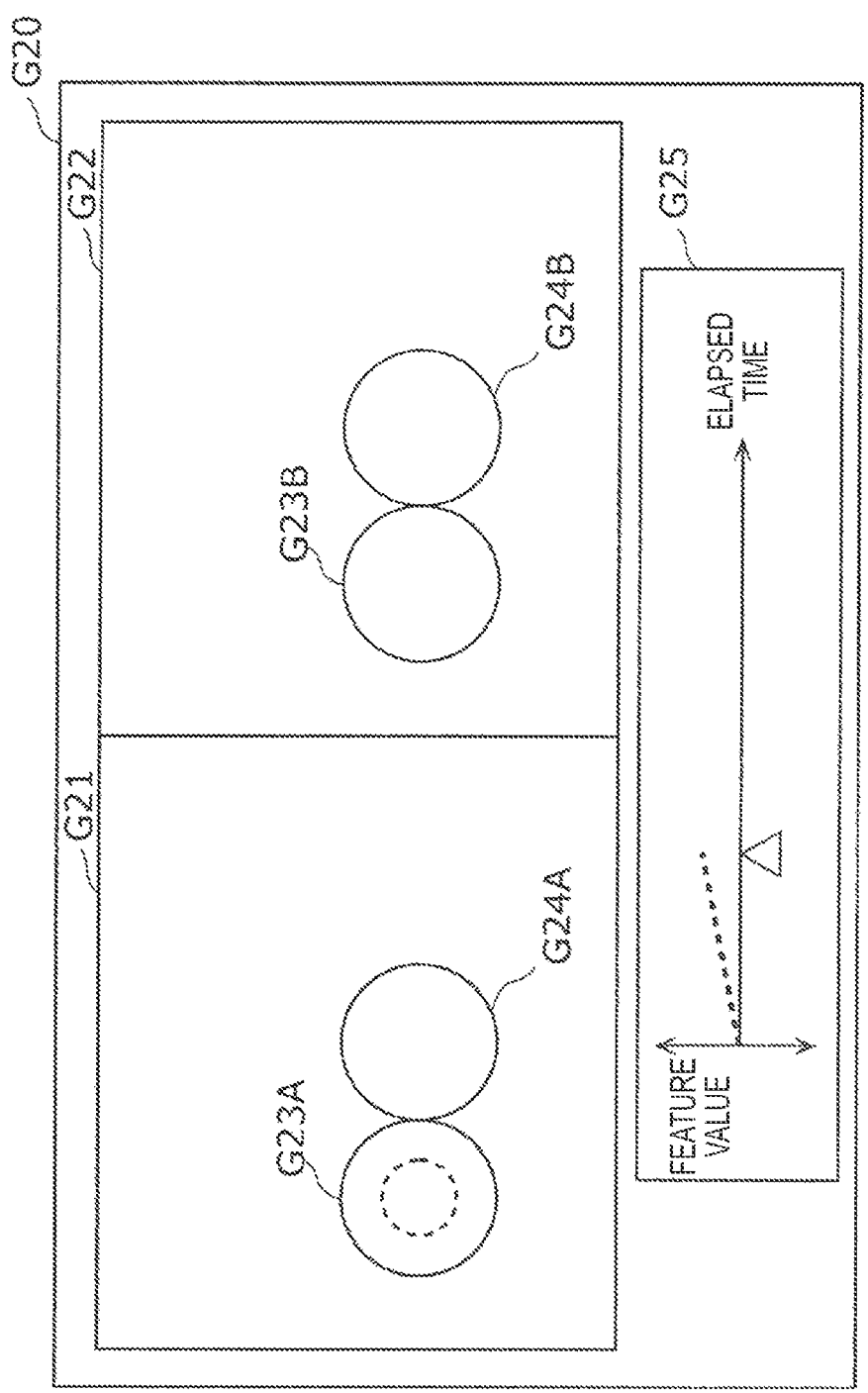
FIG. 7 is a view illustrating another example of the display screen according to the first embodiment.

FIG. 7 illustrates an example of the display screen in an imaging mode. As illustrated in FIG. 7, there are displayed on a display screen G20 (imaging mode) the contrast image G21 and the tissue image G22 corresponding to ultrasonic images, and a feature value transition G25. The contrast image G21 contains a tumor region G23A and a parenchyma region G24A. On the other hand, the tissue image G22 contains a tumor region G23B and a parenchyma region G24B.

The contrast image G21 and the tissue image G22 are the contrast image G21 and the tissue image G22 read from the data storing unit 104 and arranged in the left-right direction. The tumor regions G23A and G23B and the parenchyma regions G24A and G24B are designated by the system or the operator. The feature value transition G25 is a time-series display of feature values used for making type decision.

The display screen creating unit 108 displays the created display image on the display device 111.

[Step S202]

Then, the region of interest setting unit 105 calculates a positional deviation between the cross section of interest and the input image stored in the data storing unit 104. This positional deviation is produced by hands movement of the operator, or movements of living bodies in accordance with the heart movement and breathing. The region of interest setting unit 105 calculates the deviation based on known pattern matching. This pattern matching is executed by using the tissue image G22 formed by the image forming unit 103 in step S201 and less influenced by reflection echo from the contrast medium.

[Step S203]

Then, the region of interest setting unit 105 determines whether or not the cross section of interest and the input image after positional correction, both of which are stored in the data storing unit 104, are constituted by the same cross section. For example, the region of interest setting unit 105 calculates a discrepancy between both the images, and determines that both the images are constituted by the same cross section when the discrepancy is a threshold or smaller. When it is determined that both the images are constituted by the same cross section, the region of interest setting unit 105 corrects the positions of the regions of interest in the input image based on the deviation calculated in step S202. When it is determined that the images are constituted by different cross sections, calculation of the feature values is not performed.

[Step S204]

Then, the feature value calculating unit 106 calculates a feature value e and a feature value r used for making type decision based on the regions of interest in the input image stored in the data storing unit 104. The specific method for calculating the value e and the value r will be described later.

Figure 8:
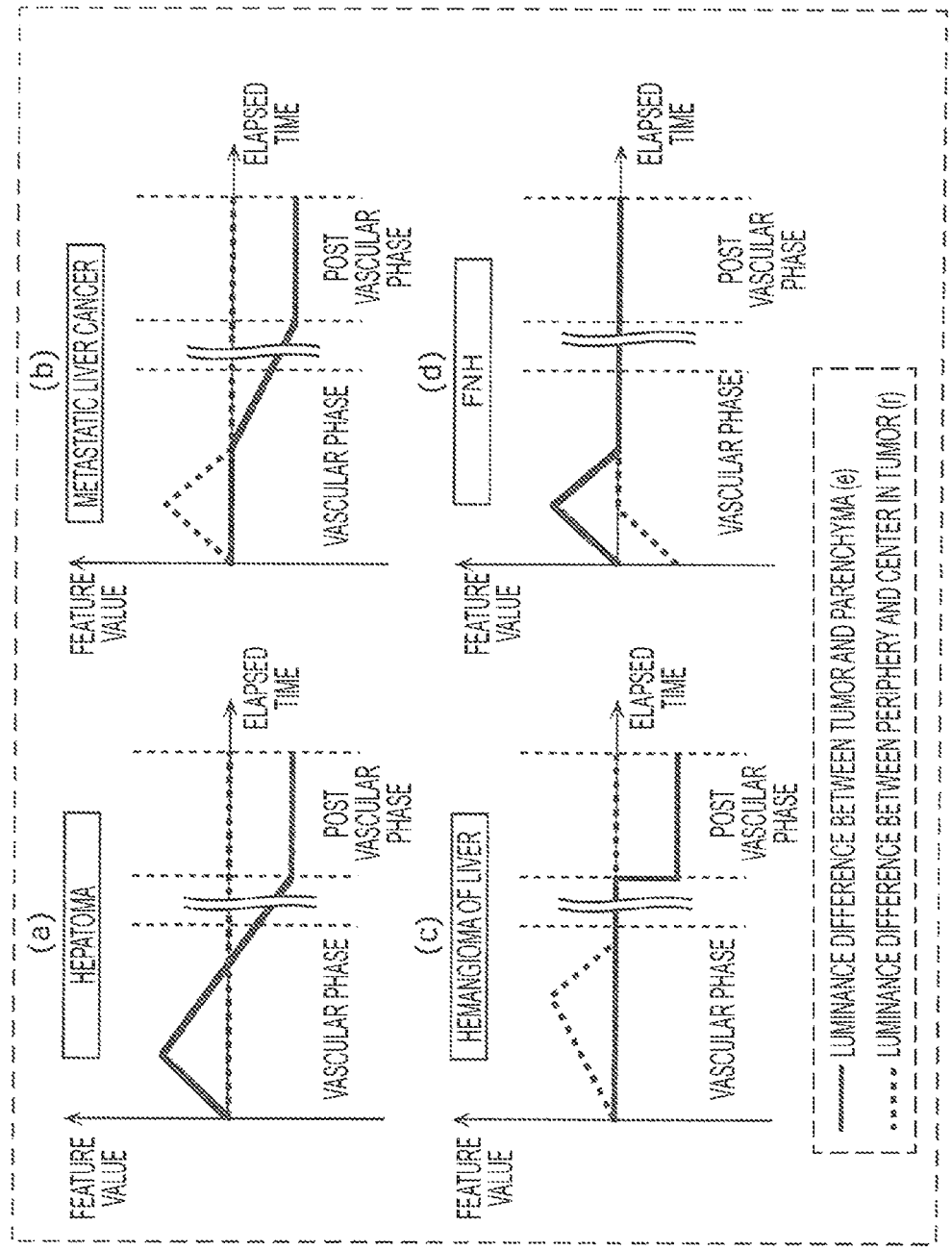
FIG. 8 is a view illustrating examples of feature values in case of a typical example of a liver tumor.

FIG. 8 is a view illustrating examples of the feature value e and the feature value r in case of a typical example of a liver tumor. In FIG. 8, the tumor region exhibits hyperechogenic with respect to the surroundings when the value e is a positive value, and exhibits hypoechogenic with respect to the surroundings when the value e is a negative value. On the other hand, the exhibited pattern is a ring pattern when the value r is a positive value, and is a center pattern when the value r is a negative value.

As illustrated in (a) in FIG. 8, hepatoma is characteristic in findings of a uniform pattern (more precisely, basket pattern) in the vascular phase, and hypoechogenic in the post vascular phase. Accordingly, the value r in the vascular phase is close to zero, while the value e in the post vascular phase is negative.

As illustrated in (b) in FIG. 8, metastatic liver cancer is characteristic in findings of a ring pattern in the vascular phase and hypoechogenic in the post vascular phase. Accordingly, the value r in the vascular phase is positive, while the value e in the post vascular phase is negative.

As illustrated in (c) in FIG. 8, hemangioma of liver is characteristic in findings of transition from a ring pattern to a uniform pattern in the vascular phase and hypoechogenic in the post vascular phase. Accordingly, the value r in the vascular phase changes from a positive value to zero, while the value e in the post vascular phase is negative.

As illustrated in (d) in FIG. 8, FNH (focal nodular hyperplasia) is characteristic in findings of a cartwheel pattern expanding from the center to the outside in the vascular phase and isoechogenic in the post vascular phase. Accordingly, the value r in the vascular phase changes from a negative value to zero, while the value e in the post vascular phase is close to zero.

As apparent from these examples, the characteristic findings of a liver tumor are supportable by the use of the value e and value r.

[Step S205]

Then, the input value acquiring unit 109 receives operation from the operator. When the operator inputs a request for ending the operation, the flow goes to step S206 to execute a process in step S206.

[Step S206]

Then, the type deciding unit 107 makes tumor type decision based on the learning data and the feature values in the range from the vascular phase to the post vascular phase stored in the data storing unit 104.

Feature values 61 for respective fixed sections of interest determined beforehand are used for making type decision.

FIG. 9 is a view illustrating tumor type decision based on feature values according to this embodiment. Sections T1 to T3 are sections of interest 60 used for type decision. Values e1 to e3, and values r1 to r3 are average values of values e and values r belonging to the respective sections of interest 60. According to an example illustrated in FIG. 9, tumor type decision is made based on six input parameters. Discussed herein is a case of type decision using a known support vector machine (linear). Assuming learning data for a type i as w(i) and b (i), an evaluation value as m(i), and an input parameter as x, a relation of (Equation 1) holds.

[Equation 1]

$$m(i) = \vec{w}(i) \cdot \vec{x} - \vec{b}(i) \qquad \text{Equation (1)}$$

In this case, the values w(i) and b(i) are learning data calculated by the support vector machine, and prepared for each type i. The details of the learning method are not described herein. In case of tumor type decision to be made for input data, the type deciding unit 107 calculates the evaluation value m(i) for all of the types, and decides, as the type of the input data, the type whose evaluation value m becomes the maximum.

The display screen creating unit 108 may display the decided type. FIG. 10 shows a screen display example of the decision results. As illustrated in this figure, the display screen creating unit 108 may display information indicating a plurality of types corresponding to decision targets, and probabilities of the respective types. The display screen creating unit 108 may display this information in a graphical manner such as a bar graph, or may display only the type which has the highest probability.

Figure 11:
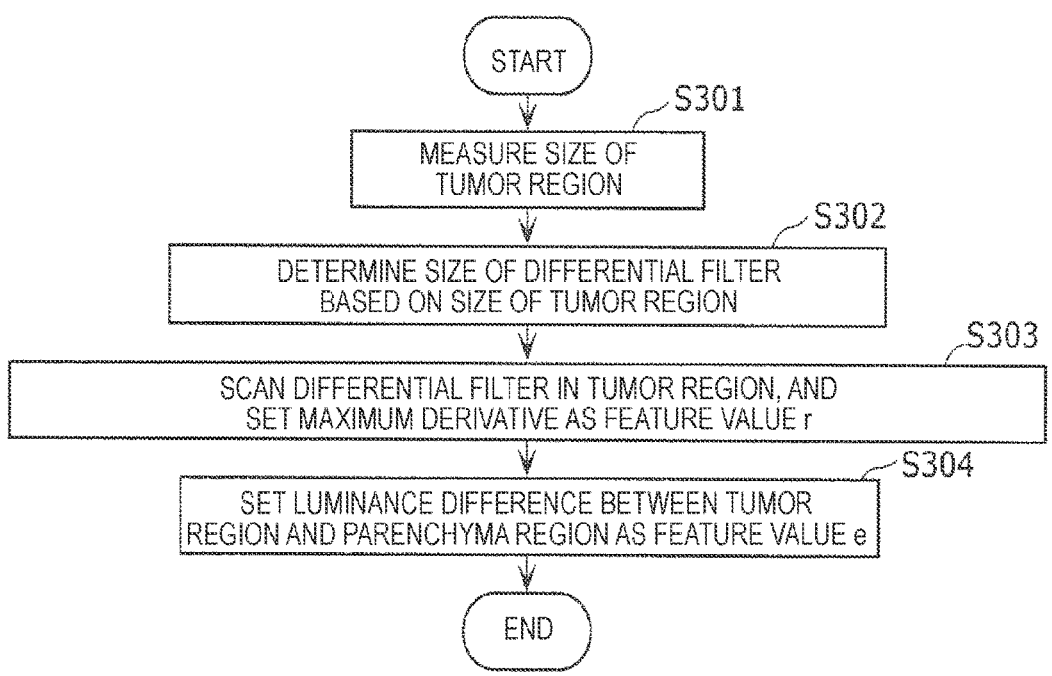
FIG. 11 is a flowchart showing feature value calculating operation according to the first embodiment.

Calculation of the feature values executed in step S204 is now described with reference to FIG. 11. FIG. 11 is a flowchart showing calculation of the feature values according to this embodiment.

[Step S301]

Figure 12A:
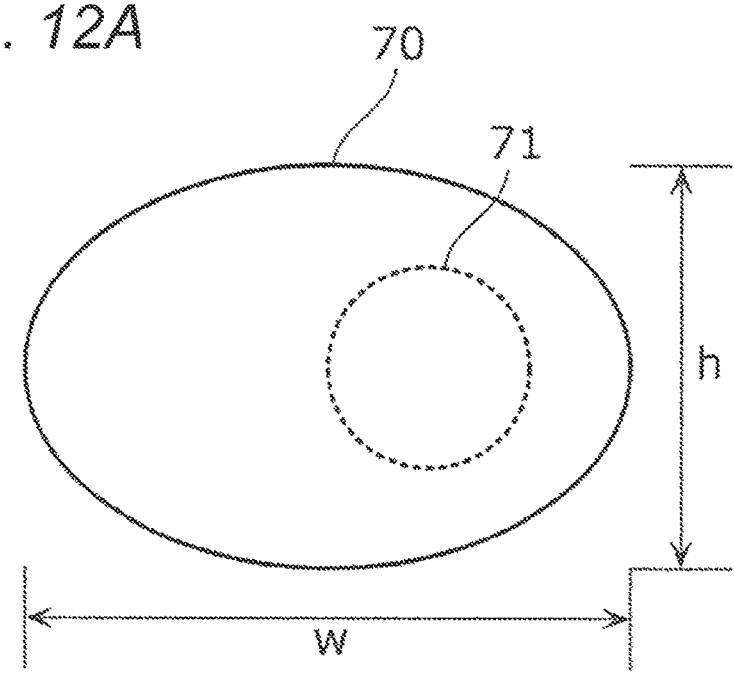
FIG. 12A is a view illustrating measurement of a size of a tumor according to the first embodiment.

Initially, the region of interest setting unit 105 measures the size of a tumor region 70 (vertical width h and horizontal width w) as illustrated in FIG. 12A.

[Step S302]

Figure 12B:
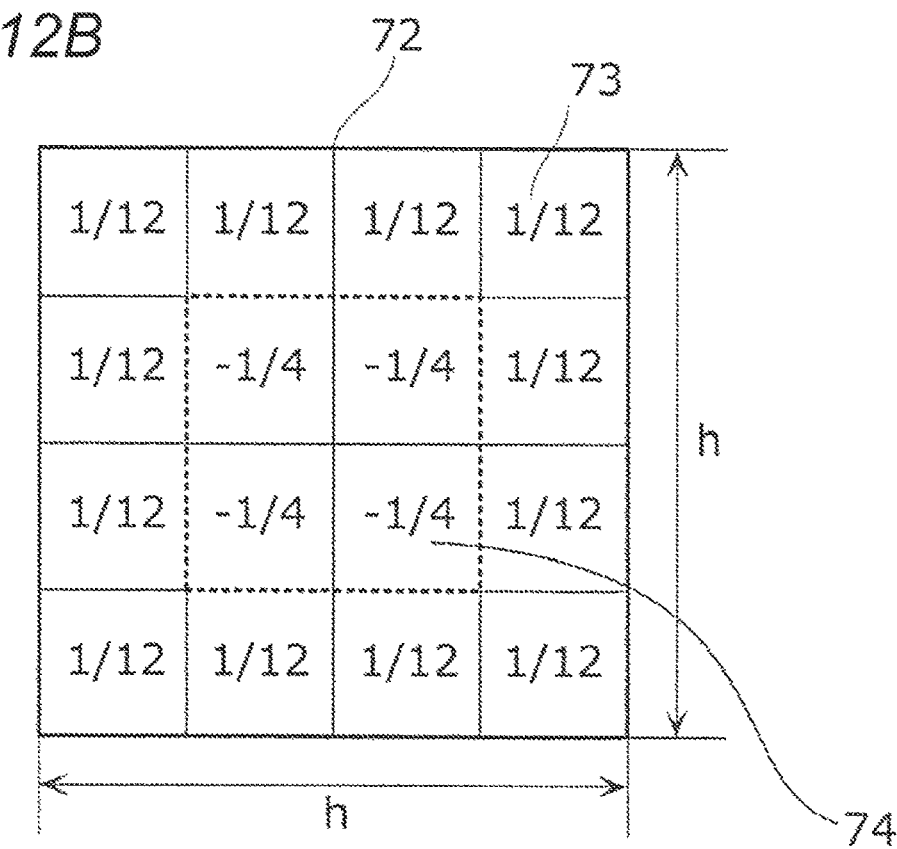
FIG. 12B is a view illustrating size setting of a differential filter according to the first embodiment.

Then, the region of interest setting unit 105 determines the size of a differential filter 72 based on the measured tumor size. The differential filter 72 is provided for detecting a ring pattern. As illustrated in FIG. 12B, a coefficient 74 at the center of the differential filter 72 is negative, while a coefficient 73 in the periphery is positive. The former region having the negative coefficient corresponds to a first region of interest in a central portion of the ring pattern of the tumor region 70, while the latter region having the positive coefficient corresponds to a second region of interest in a peripheral portion of the ring pattern of the tumor region 70.

According to the example illustrated in FIG. 12B, the size of the differential filter 72 has a length corresponding to the vertical width of the tumor region 70, i.e., the vertical width smaller than the horizontal width of the tumor region 70. The shape of the differential filter 72 is a square shape. The size of the negative region is half the size of each of the vertical and horizontal widths of the differential filter 72. However, the size of the negative region is not limited to this size. It is preferable that the size of the negative region lies approximately in the range from half the size of each of the vertical and horizontal widths of the differential filter 72 to three fourths of the size of each of the vertical and horizontal widths of the differential filter 72.

[Step S303]

Figure 13A:
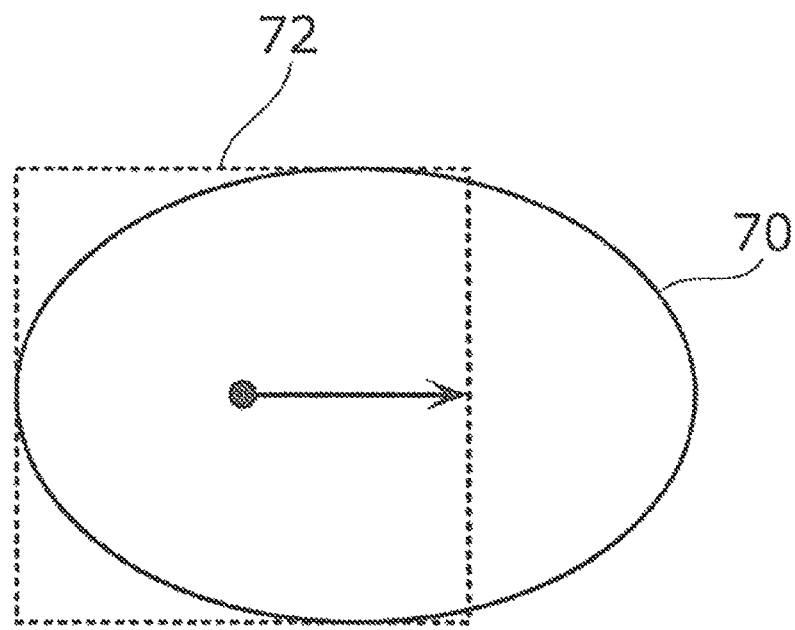
FIG. 13A is a view illustrating an example of the differential filter and a shift range of the differential filter according to the first embodiment.

Then, the feature value calculating unit 106 shifts the differential filter 72 within the tumor region 70 as illustrated in FIG. 13A, and performs product-sum operation for the differential filter 72 and the image at each position to obtain derivatives. More specifically, assuming a pixel value as p, a coefficient value of the differential filter 72 as f, and the size (range) of the differential filter 72 as R, a derivative d at a position (x, y) in the image is expressed as the following (Equation 2).

[Equation 2]

$$d(x, y) = \sum_{i,j \in R} p(x+i, y+j) \cdot f(i, j) \quad \text{Equation (2)}$$

Then, the feature value calculating unit 106 sets the maximum derivative d in the plurality of calculated derivatives d as the value r (feature value r) corresponding to an image feature value. More specifically, assuming that a scan range within the tumor region 70 is S, the value r is expressed as the following (Equation 3).

[Equation 3]

$$r = \underset{x,y \in S}{\text{MAX}}[d(x, y)] \quad \text{Equation (3)}$$

By this method, the feature value calculating unit 106 can extract the feature value at the position where the ring pattern is most prominent within the tumor region 70.

[Step S304]

Finally, the feature value calculating unit 106 calculates an average luminance value for each of the tumor region 70 and parenchyma region, and sets the difference between these average values as the value e (feature value e) corresponding to an image feature value. In this case, the feature value calculating unit 106 may calculate, as the average luminance value of the tumor region 70, an average luminance value in the image region where the maximum feature value d is calculated (in the same size as the size R of the differential filter 72), or an average luminance value of the entire tumor region detected or set in step S104.

Assuming the average luminance of the tumor region 70 as x, and the average luminance of the parenchyma region as y, the value e is expressed by the following (Equation 4).

[Equation 4]

$$e = x - y \quad \text{Equation (4)}$$

Figure 13B:
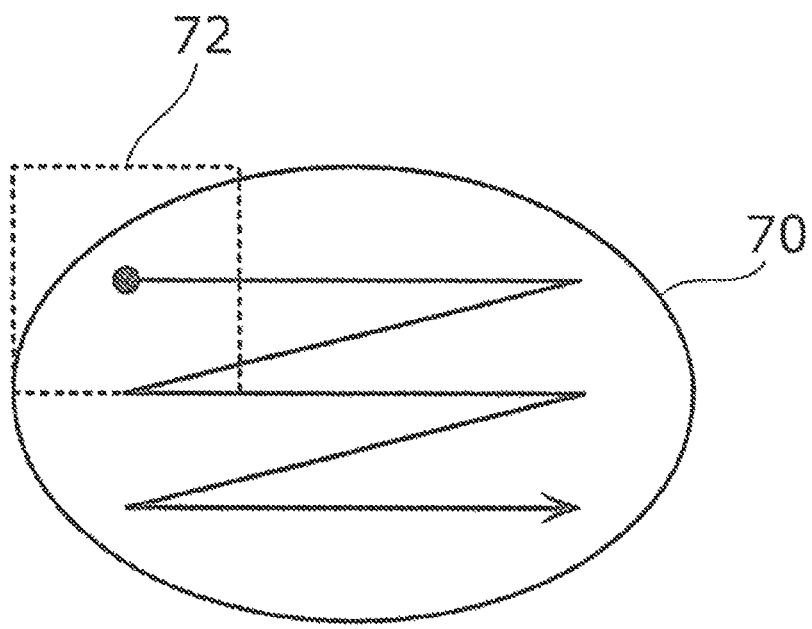
FIG. 13B is a view illustrating another example of the differential filter and the shift range of the differential filter according to the first embodiment.
Figure 13C:
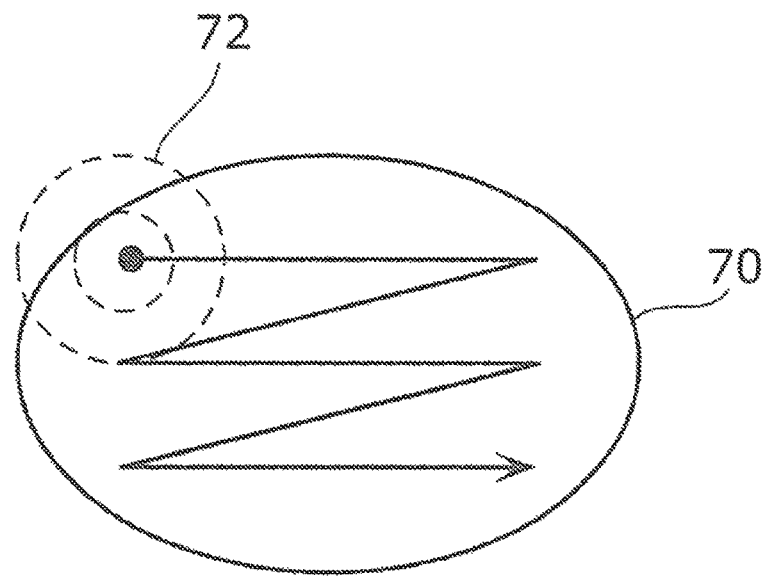
FIG. 13C is a view illustrating a further example of the differential filter and the shift range of the differential filter according to the first embodiment.

The feature value calculating unit 106 may set the size of the differential filter 72 to a further smaller size than the smaller width of either the vertical width or horizontal width of the tumor region 70 so as to conduct finer scanning for the inside of the tumor region 70 as illustrated in FIG. 13B. In addition, the shape of the differential filter 72 may be a circular shape or an approximately circular shape as illustrated in FIG. 13C.

The feature value calculating unit 106 may scan the differential filter 72 only when the luminance of the tumor region 70 becomes a predetermined threshold or higher. This method initiates scanning prior to the time of contrast, wherefore the detection results do not become instable.

The feature value calculating unit 106 may conduct this scanning only for a predetermined time phase (such as artery phase), and apply the position of the differential filter 72 determined in the predetermined time phase to the following time phases, for example. This method prevents shift of the determined position of the differential filter 72 in the subsequent time phases.

According to the foregoing example, the value r is the difference between the luminance value in the peripheral portion where the positive coefficients of the differential filter 72 are integrated, and the luminance value at the central portion where the negative coefficients of the differential filter 72 are integrated. However, the value r may be a luminance difference between the luminance value in the central portion, and the luminance value in a region contained in the tumor region 70 and corresponding to a portion other than the central portion.

The display screen creating unit 108 may display the position where the derivative d becomes the maximum. For example, the display screen creating unit 108 draws a substantially circular shape to indicate the outer edge of the central portion, i.e., the boundary between the central portion where the negative regions of the differential filter 72 are integrated, and the peripheral portion where the positive regions of the differential filter 72 are integrated. The display screen creating unit 108 may also draw a substantially circular shape to indicate the outer edge of the peripheral portion. This method allows the operator to recognize which position in the tumor region has been extracted as the central portion of the ring pattern. The display screen creating unit 108 may display the central portion and the peripheral portion only when the value r is larger than a predetermined threshold. This method allows the operator to recognize the situations in deciding likelihood of the ring pattern.

The display screen creating unit 108 may display the position of the differential filter 72 during scanning in step S303. In addition, buttons or bars for play, pause and the like may be equipped. Moreover, the operator may shift or fix the position of the differential filter 72, or modify the shape of the differential filter 72 by dragging the mouse on the outer edge of the central portion or the peripheral portion. Particularly, during offline operation of the ultrasonic diagnostic apparatus 100, correction of the position of the differential filter 72 increases the accuracy of the features of the tumor region 70 obtained based on observation and experiences of the operator. As a result, the accuracy of the type decision results improves.

Discussed hereinabove is the flowchart of the operation executed after administration of the contrast medium according to this embodiment.

According to the description hereinabove, the candidate for the parenchyma region is set to a region located at the same depth as the depth of the tumor region and close to the tumor region. However, the candidate for the parenchyma is not limited to this region. For example, such a region may be selected which has a depth different from the depth of the tumor region when there exists a hyperechogenic region such as the diaphragm in the region located at the same depth as the depth of the tumor region and close to the tumor region.

In calculating the luminance difference between the tumor region and the parenchyma region, the feature value calculating unit 106 is not required to calculate the luminance value of the tumor region based on the luminance value of the entire tumor region, but may calculate the luminance value of the tumor region based on the luminance value of a hypoechogenic region 71 used for calculation of the feature values of the ring pattern, for example.

According to the above description, the feature value calculating unit 106 uses the average luminance of each of the regions for calculation of the feature values. However, other information on luminance may be used for this purpose. Other information on luminance in this context may include luminance at a point of a predetermined position within the region, the center value of luminance of the region, or a mode of luminance in the region, for example.

The type deciding unit 107 may vary the sections of interest 60 for each type of tumors when associating feature values with tumor types.

According to the foregoing example, the type deciding unit 107 uses the support vector machine when associating feature values with tumor types. However, the type deciding unit 107 is not required to use the support vector machine but may adopt other types of machine learning.

Advantageous Effects

As described above, the ultrasonic diagnostic apparatus according to an aspect of the present invention can decide a tumor type based on a luminance difference between two regions of interest contained in a target region (tumor region) in an ultrasonic image and exhibiting remarkable features for each type of the tumor. More specifically, the ultrasonic diagnostic apparatus decides a ring pattern based on the luminance difference between the two regions of interest, and thereby evaluates the degree of the ring pattern. In this case, the ultrasonic diagnostic apparatus more appropriately identifies a tumor type. Accordingly, the ultrasonic diagnostic apparatus can decide a type of a liver tumor with high accuracy without depending on a person who reads images.

The ultrasonic diagnostic apparatus searches for a region where the degree of the ring pattern becomes the maximum within a tumor region. Accordingly, the ultrasonic diagnostic apparatus can appropriately calculate the degree of the ring pattern even when the ring pattern is not present at the center of the tumor region.

The ultrasonic diagnostic apparatus decides a tumor type based on the luminance difference between a tumor region and a parenchyma region in an ultrasonic image, as well as on the luminance of the tumor region. Accordingly, the ultrasonic diagnostic apparatus can decide a type of a liver tumor with high accuracy.

The ultrasonic diagnostic apparatus recognizes a tumor region in an ultrasonic image as a circular shape, and sets a region of interest for each of the central portion the circular shape and the peripheral portion of the circular shape. Then, the ultrasonic diagnostic apparatus calculates the luminance difference between these regions of interest to identify the type of the tumor based on the luminance difference. Accordingly, the ultrasonic diagnostic apparatus can decide a type of a liver tumor with higher accuracy.

The search for the ring pattern may be limited to the artery phase. More specifically, the region of interest setting unit 105 sets the first region of interest in an ultrasonic image in the artery phase. The feature value calculating unit 106 calculates a ring level (feature value r) for each of a plurality of time phases based on the set first region of interest. The ring level in this context refers to the degree of the ring pattern. The type deciding unit 107 decides a tumor type based on the plurality of calculated ring levels. Accordingly, the ultrasonic diagnostic apparatus can prevent shift of the evaluation position in the ring pattern for each time phase, thereby deciding a type of a liver tumor with high accuracy.

The ultrasonic diagnostic apparatus displays the positions of regions of interest in an image, i.e., positions to which the differential filter 72 is applied for calculation of the feature value r of the ring pattern. Accordingly, the operator can recognize validity of type decision.

Second Embodiment

According to the first embodiment discussed above, the feature value calculating unit 106 searches for a region where the derivative becomes the maximum. However, the feature value calculating unit 106 in this embodiment searches for a region where a luminance value becomes the minimum.

Figure 14:
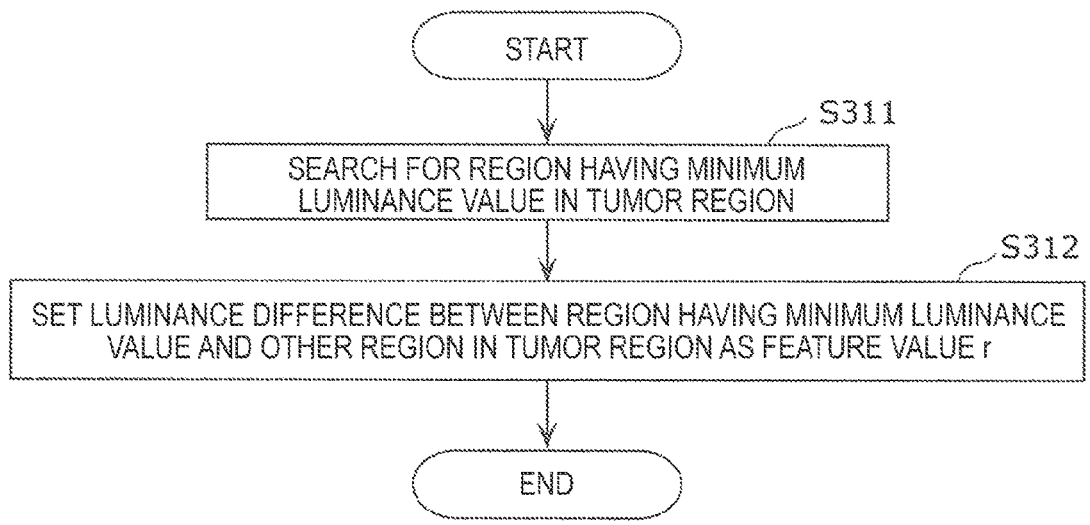
FIG. 14 is a flowchart showing feature value calculating operation according to a second embodiment.
Figure 15:
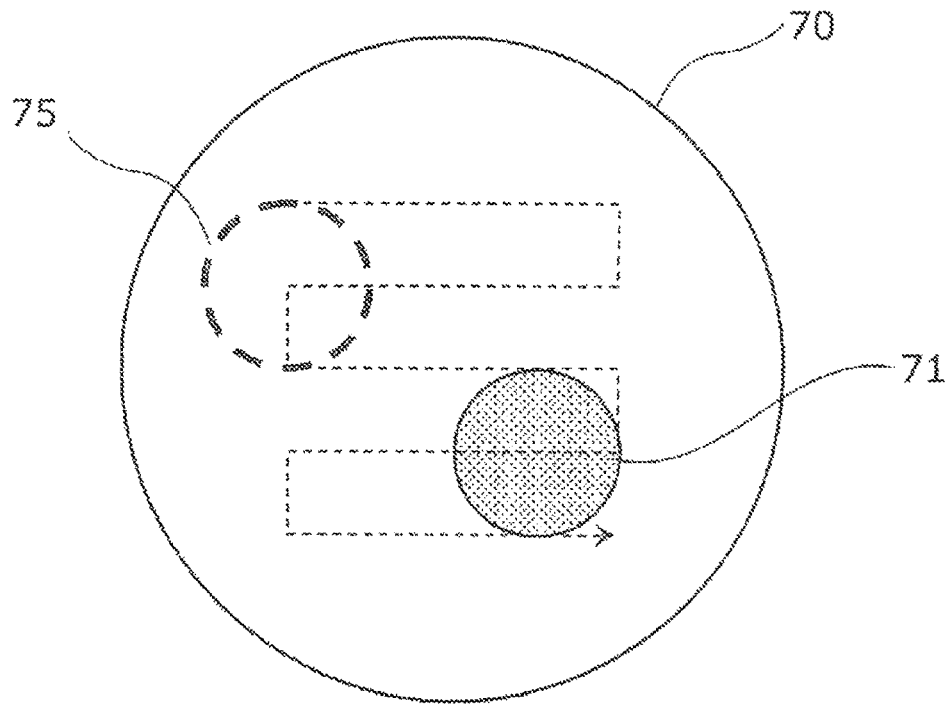
FIG. 15 is a view illustrating the feature value calculating operation according to the second embodiment.

FIG. 14 is a flowchart showing a feature value calculating process according to this embodiment.

As illustrated in FIG. 14, the feature value calculating unit 106 searches for a region where a luminance value becomes the minimum within a tumor region (S311). More specifically, the feature value calculating unit 106 scans a search region 75 in the tumor region 70 to search for a region where the luminance value becomes the minimum as illustrated in FIG. 5. The luminance value in this context refers to an average of luminance values within the search region 75, for example. The luminance value may be a center value or a mode of the luminance values in the search region 75, for example. The size of the search region 75 is approximately equivalent to the size of the region corresponding to the coefficient 74 at the center of the differential filter 72, for example.

Then, the feature value calculating unit 106 calculates the luminance difference between the luminance value of the region where the luminance value becomes the minimum, and the luminance value of a region contained in the tumor region 70 and corresponding to a portion other than the region where the luminance value becomes the minimum, and sets the calculated luminance difference to the feature value r (S312).

As discussed above, the ultrasonic diagnostic apparatus according to this embodiment searches for the region where the luminance value becomes the minimum within the tumor region. Accordingly, the ultrasonic diagnostic apparatus can appropriately calculate the degree of a ring pattern even when the ring pattern is not present at the center of the tumor region.

Third Embodiment

Discussed in this embodiment is a modified example of the method for calculating the feature value r.

Figure 16:
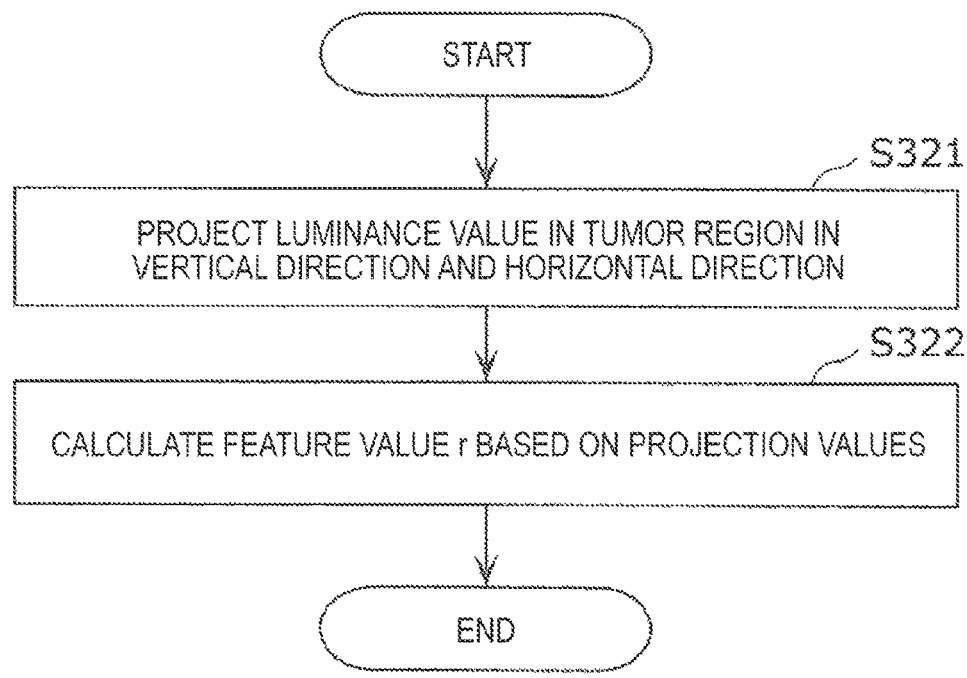
FIG. 16 is a flowchart showing feature value calculating operation according to a third embodiment.

FIG. 16 is a flowchart showing a feature value calculating process according to this embodiment.

Figure 17:
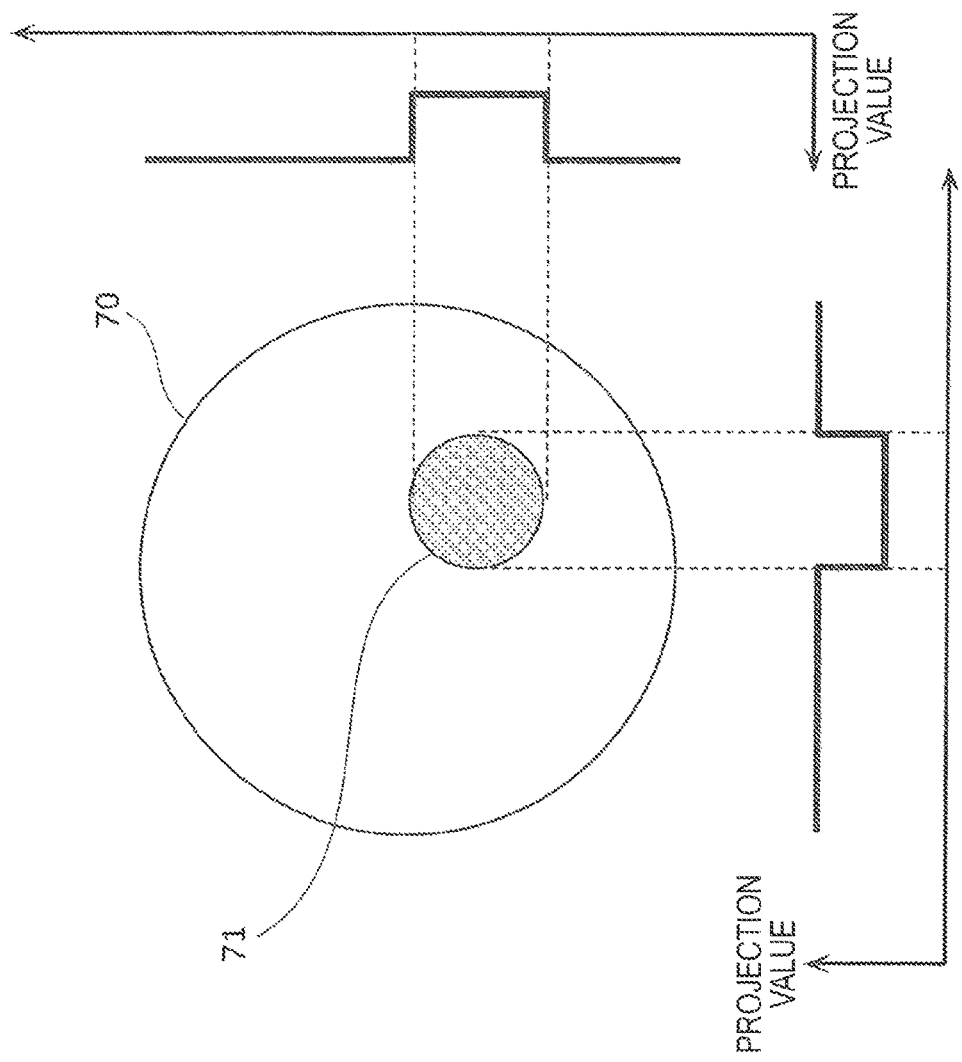
FIG. 17 is a view illustrating the feature value calculating operation according to the third embodiment.

Initially, the feature value calculating unit 106 projects a luminance value of the tumor region 70 in the vertical direction and the horizontal direction as illustrated in FIG. 17 (S321). Projecting a luminance value in the vertical direction in this context refers to a process for calculating an average of luminance values of a plurality of pixels contained in pixel columns for each of the pixel columns in the tumor region 70. Similarly, projecting a luminance value in the horizontal direction in this context refers to a process for calculating an average of luminance values of a plurality of pixels contained in pixel rows for each of the pixel rows in the tumor region 70. This process may be executed for each pixel, or may be executed for each region containing a plurality of pixels. Alternatively, a center value or an aspect may be used in place of the average value.

Then, the feature value calculating unit 106 calculates the feature value r based on a projection value in the vertical direction and a projection value in the horizontal direction (S322). More specifically, the feature value calculating unit 106 obtains a degree of downward convexity for each of the projection value in the vertical direction and the projection value in the horizontal direction, and sets the respective degrees of downward convexity as feature values. For example, the feature value calculating unit 106 fits each of the projection values to a function convex downward (such as quadratic function). More specifically, the feature value calculating unit 106 determines a quadratic function most fitted to the projection values for each while varying coefficient value of the quadratic function. Then, the feature value calculating unit 106 sets the coefficient value of the x-squared term of the determined quadratic function to the feature value r. In this case, the feature value r increases (the degree of the ring shape increases) as the degree of the downward convexity of the projection value increases.

As discussed above, the ultrasonic diagnostic apparatus according to this embodiment decides the degree of the ring pattern based on the projection values of the luminance values in the tumor region. Accordingly, the ultrasonic diagnostic apparatus can appropriately calculate the degree of the ring pattern even when the ring pattern is not present at the center of the tumor region.

Fourth Embodiment

Discussed in this embodiment is a modified example of the method for calculating the feature value r.

Figure 18:
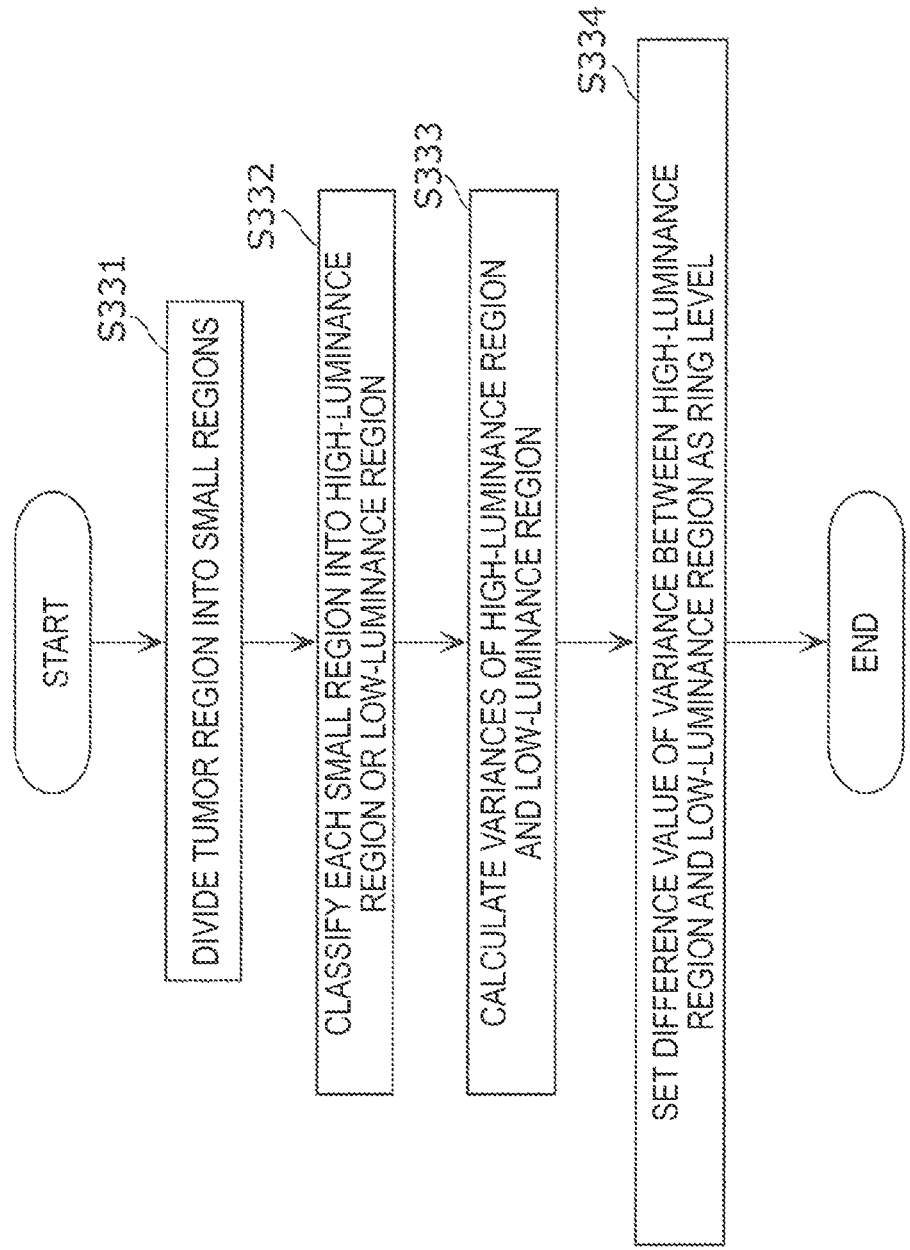
FIG. 18 is a flowchart showing feature value calculating operation according to a fourth embodiment.

FIG. 18 is a flowchart showing a feature value calculating process according to this embodiment.

Figure 19:
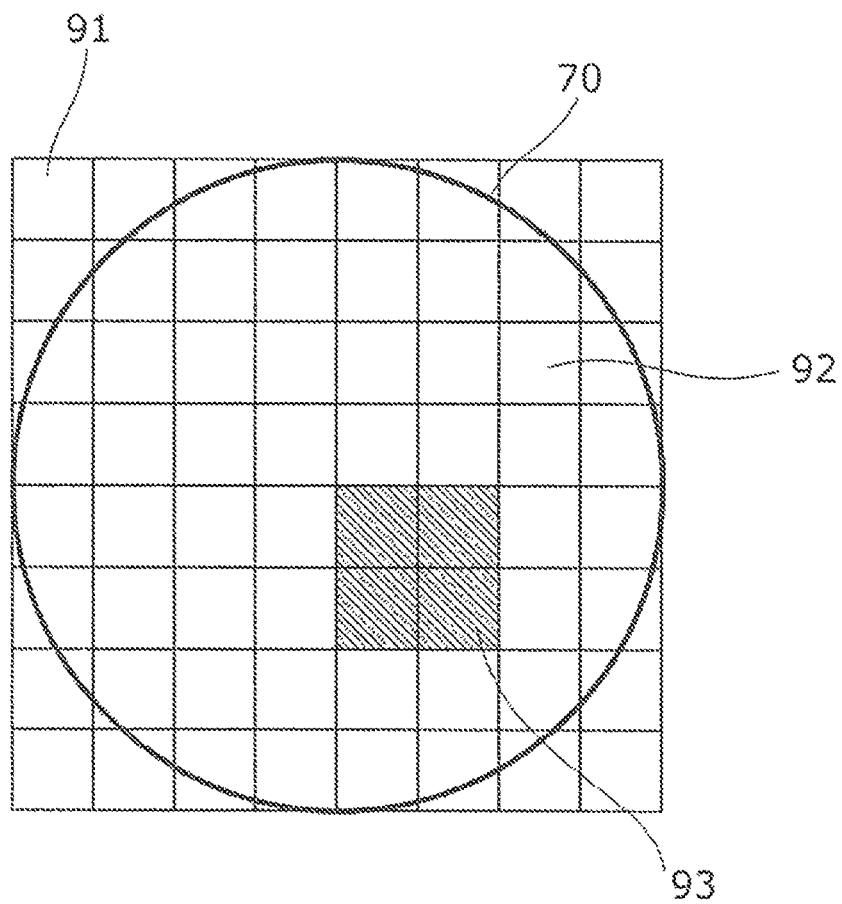
FIG. 19 is a view illustrating the feature value calculating operation according to the fourth embodiment.

Initially, the feature value calculating unit 106 divides the tumor region 70 into a plurality of small regions 91 as illustrated in FIG. 19 (S331). Each of the small regions 91 herein contains a plurality of pixels. Each of the small regions 91 may contain only one pixel. In other words, the following process may be executed for each pixel without performing this region dividing process.

Then, the feature value calculating unit 106 classifies each of the small regions into a high-luminance region 92 or a low-luminance region 93 (S332). The high-luminance region 92 in this context refers to a region having a luminance value (such as average value, center value, and mode) higher than each luminance value of the low-luminance region 93. For example, discriminant analysis method or K-means (K-means) may be adopted for this classification.

Then, the feature value calculating unit 106 calculates a variance Vh at the positions of the high-luminance regions 92, and a variance Vl at the positions of the low-luminance regions 93 (S333). More specifically, the variance Vh is a value calculated by dividing the sum of squares of the differences between the average coordinates (center coordinates) at the positions of the plurality of high-luminance regions 92 and the respective high-luminance regions 92 by the total number of the high-luminance regions 92. Similarly, the variance Vl is a value calculated by dividing the sum of squares of the differences between the average coordinates (center coordinates) at the positions of the plurality of low-luminance regions 93 and the respective low-luminance regions 93 by the total number of the low-luminance regions 93.

Then, the feature value calculating unit 106 sets the difference between the variance Vh and the variance Vl to the ring level (feature value r) (S334). More specifically, the feature value r is expressed as Vh−Vl. In other words, the feature value r (ring level) becomes a large value at the time of a small value of the variance Vl for the low-luminance regions and a large value of the variance Vh for the high-luminance regions 92.

As described above, the ultrasonic diagnostic apparatus according to this embodiment decides the degree of the ring pattern based on the variances of the high-luminance regions and the low-luminance regions. Accordingly, the degree of the ring pattern can be appropriately calculated even when the ring pattern is not present at the center of the tumor region.

Fifth Embodiment

Discussed in this embodiment is a modified example of the method for calculating the feature value r.

Figure 20:
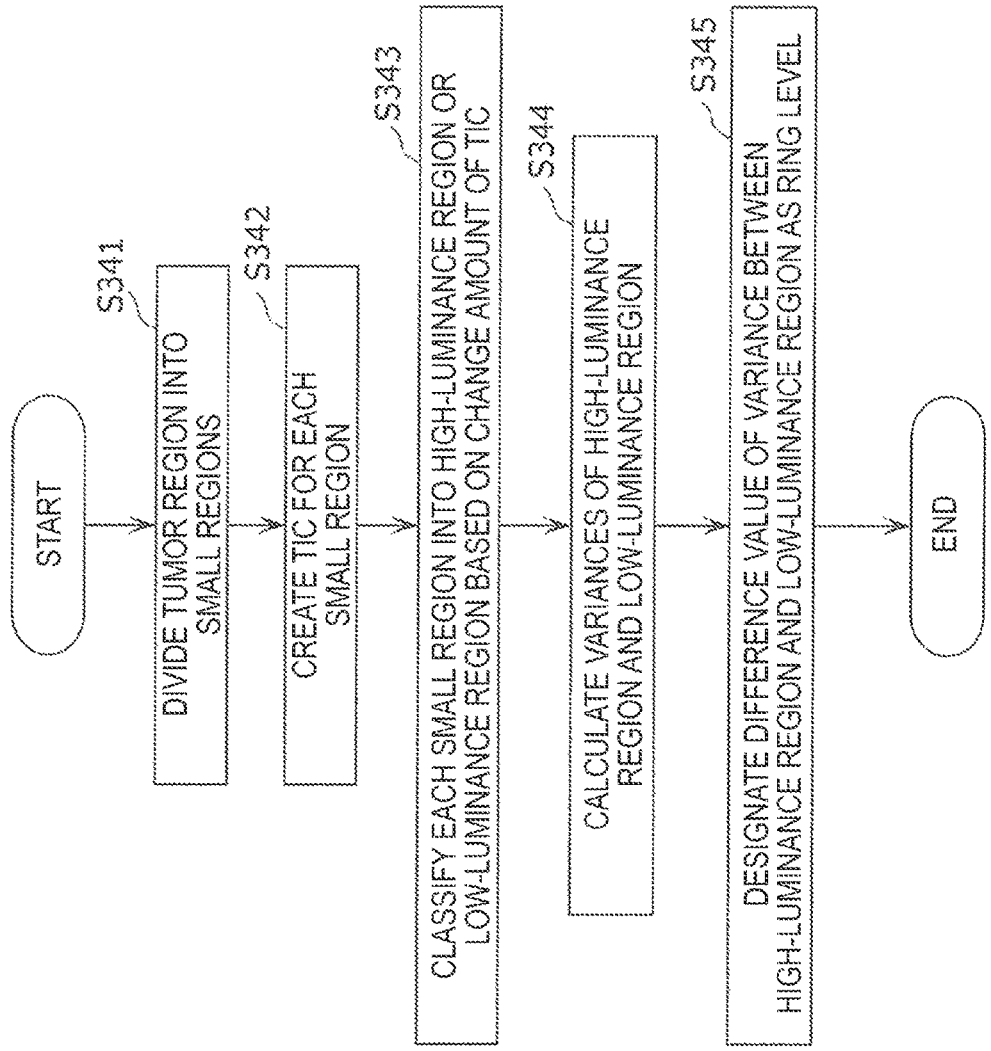
FIG. 20 is a flowchart showing feature value calculating operation according to a fifth embodiment.

FIG. 20 is a flowchart showing a feature value calculating process according to this embodiment.

Figure 21:
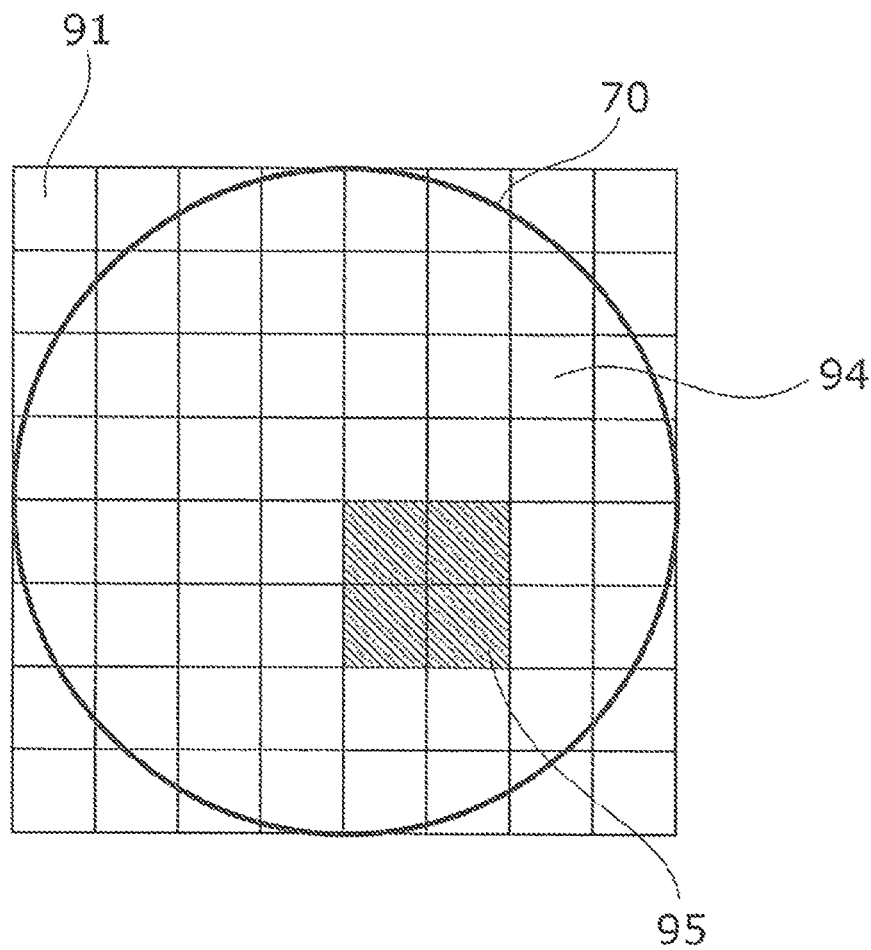
FIG. 21 is a view illustrating the feature value calculating operation according to the fifth embodiment.

Initially, the feature value calculating unit 106 divides the tumor region 70 into the plurality of small regions 91 as illustrated in FIG. 21 (S341). This process is similar to the process in S331 shown in FIG. 18.

Figure 22A:
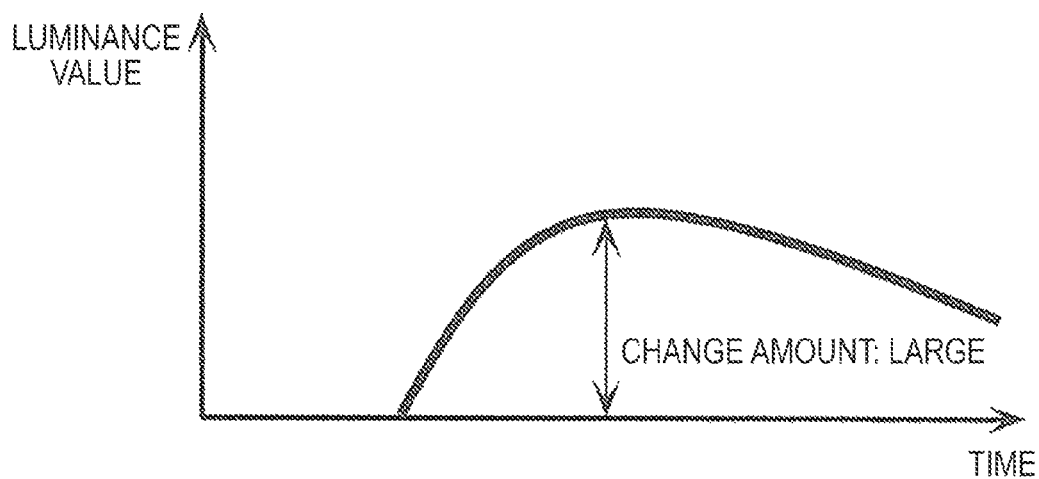
FIG. 22A is a view illustrating an example of a TIC according to the fifth embodiment.
Figure 22B:
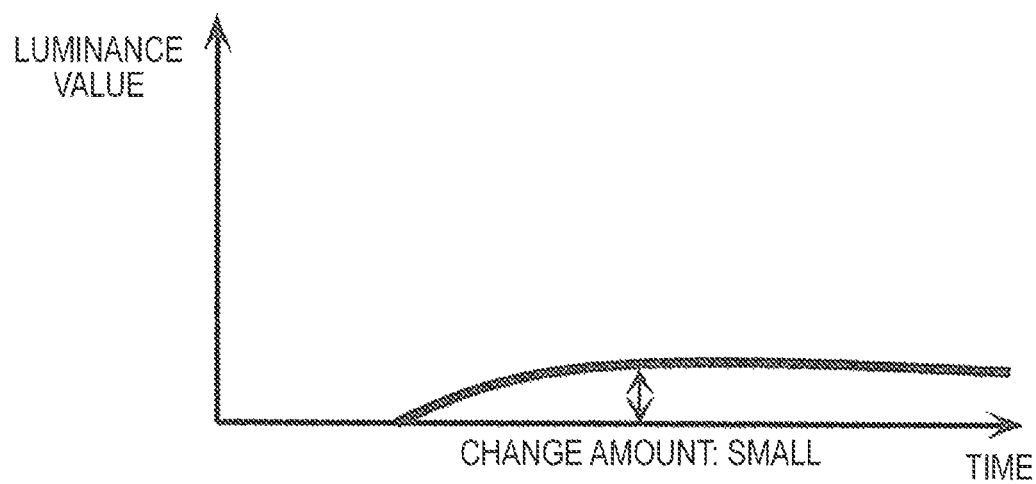
FIG. 22B is a view illustrating an example of the TIC according to the fifth embodiment.

Then, the feature value calculating unit 106 creates a TIC (Time Intensity Curve) for each of the small regions 91 (S342). Each of the TICs herein shows a change of the luminance value with time as illustrated in FIGS. 22A and 22B.

Then, the feature value calculating unit 106 classifies each of the small regions 91 into a high-luminance region 94 or a low-luminance region 95 (S343) based on the change amount of the TIC. The change amount in this context refers to a difference between the maximum luminance value and the minimum luminance value in the TIC. The feature value calculating unit 106 classifies the target small region 91 into the high-luminance region 94 when the change amount of the region is larger than a predetermined threshold, and classifies the target small region 91 into the low-luminance region 95 when the change amount of the region is smaller than the predetermined threshold.

Then, the feature value calculating unit 106 calculates the variance Vh at the positions of the high-luminance regions 94, and the variance Vl at the positions of the low-luminance regions 95 (S344).

Then, the feature value calculating unit 106 sets the difference between the variance Vh and the variance Vl to the ring level (feature value r) (S345). More specifically, the feature value r is expressed as Vh−Vl. In other words, the feature value r (ring level) becomes a large value at the time of a small value of the variance Vl for the low-luminance regions and a large value of the variance Vh for the high-luminance regions.

As described above, the ultrasonic diagnostic apparatus according to this embodiment decides the degree of the ring pattern based on the variances of the high-luminance regions and the low-luminance regions. Accordingly, the degree of the ring pattern can be appropriately calculated even when the ring pattern is not present at the center of the tumor region.

CONCLUSION

Figure 23:
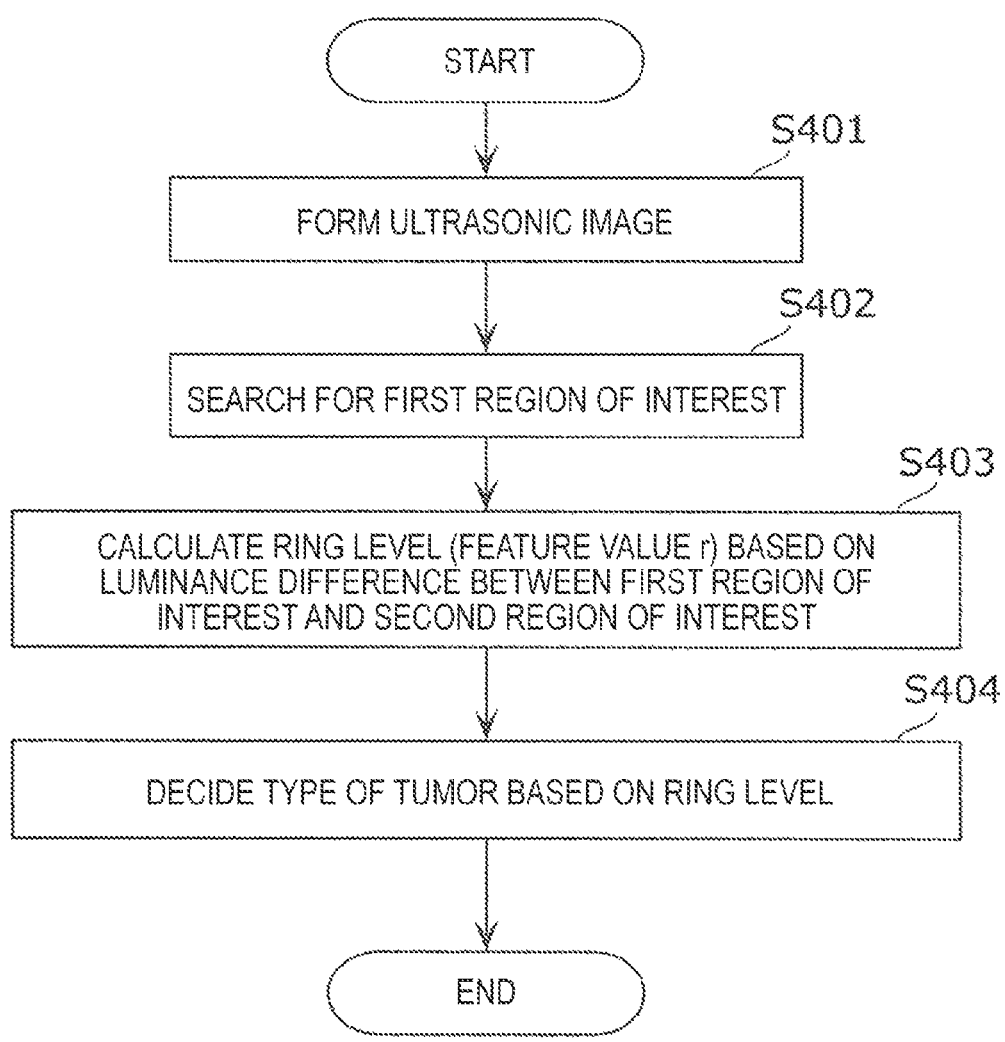
FIG. 23 is a flowchart showing operation executed by the ultrasonic diagnostic apparatus according to the first embodiment and an ultrasonic diagnostic apparatus according to the second embodiment.

As described in the first embodiment and the second embodiment, the ultrasonic diagnostic apparatus according to an aspect of the present invention executes a process shown in FIG. 23. Initially, the image forming unit 103 forms an ultrasonic image corresponding to echo signals received from a specimen after administration of a contrast medium (S401).

Then, the region of interest setting unit 105 searches for the first region of interest from the inside of a tumor region containing a tumor in the ultrasonic image. The first region of interest corresponds to a center portion having a lower luminance value in a ring shape than the luminance value of a peripheral portion surrounding the central portion (S402).

More specifically, as discussed in the first embodiment, the region of interest setting unit 105 searches for a first region and a second region where the luminance difference becomes the maximum. In more detail, the region of interest setting unit 105 searches for a search region where the luminance difference between the first region and the second region becomes the maximum in a plurality of search regions in a predetermined size contained in the tumor region and located at different positions. Then, the region of interest setting unit 105 sets the first region contained in the search region exhibiting the maximum luminance difference to the first region of interest. In this case, the first region is a range determined beforehand in the search region (differential filter 72), and corresponds to the region of the coefficient 74 at the center of the differential filter 72. On the other hand, the second region is a range determined beforehand in the search region and surrounding the first region, and corresponds to the region of the coefficient 73 in the periphery of the differential filter 72.

The first region may be substantially circular, while the second region may be a substantially circular region centered at the center of the first region and corresponding to a portion other than the first region.

As discussed in the second embodiment, the region of interest setting unit 105 may search for a region where the luminance becomes the minimum. More specifically, the region of interest setting unit 105 may search for a search region exhibiting the minimum luminance in the plurality of search regions in a predetermined size contained in the tumor region and located at different positions, and sets the search region exhibiting the minimum luminance to the first region of interest.

Then, the feature value calculating unit 106 calculates the difference between the luminance of the first region of interest and the luminance of the second region of interest corresponding to a peripheral portion to designate the difference as a ring level (feature value r) indicating the degree of a ring shape in the image of the tumor region (S403). In this case, the second region of interest is a portion of the tumor region other than the first region of interest. As discussed in the first embodiment, the second region of interest may be constituted by the second region when the search is conducted based on the luminance difference between the first region and the second region.

Then, the type deciding unit 107 decides the tumor type based on the ring level (S404).

The foregoing search process (S402) may be executed for each of the plurality of ultrasonic images, or may be executed for only a part of the ultrasonic images. When the search process is executed for only a part of the ultrasonic images, the first region of interest searched in the search process is applied to the other ultrasonic images. For example, the image forming unit 103 forms ultrasonic images for a plurality of time phases including an artery phase. The region of interest setting unit 105 sets the first region of interest in the ultrasonic image for the artery phase. The feature value calculating unit 106 calculates a plurality of ring levels for the plurality of time phases based on the set first region of interest. The type deciding unit 107 decides the tumor type based on the plurality of calculated ring levels.

Figure 24:
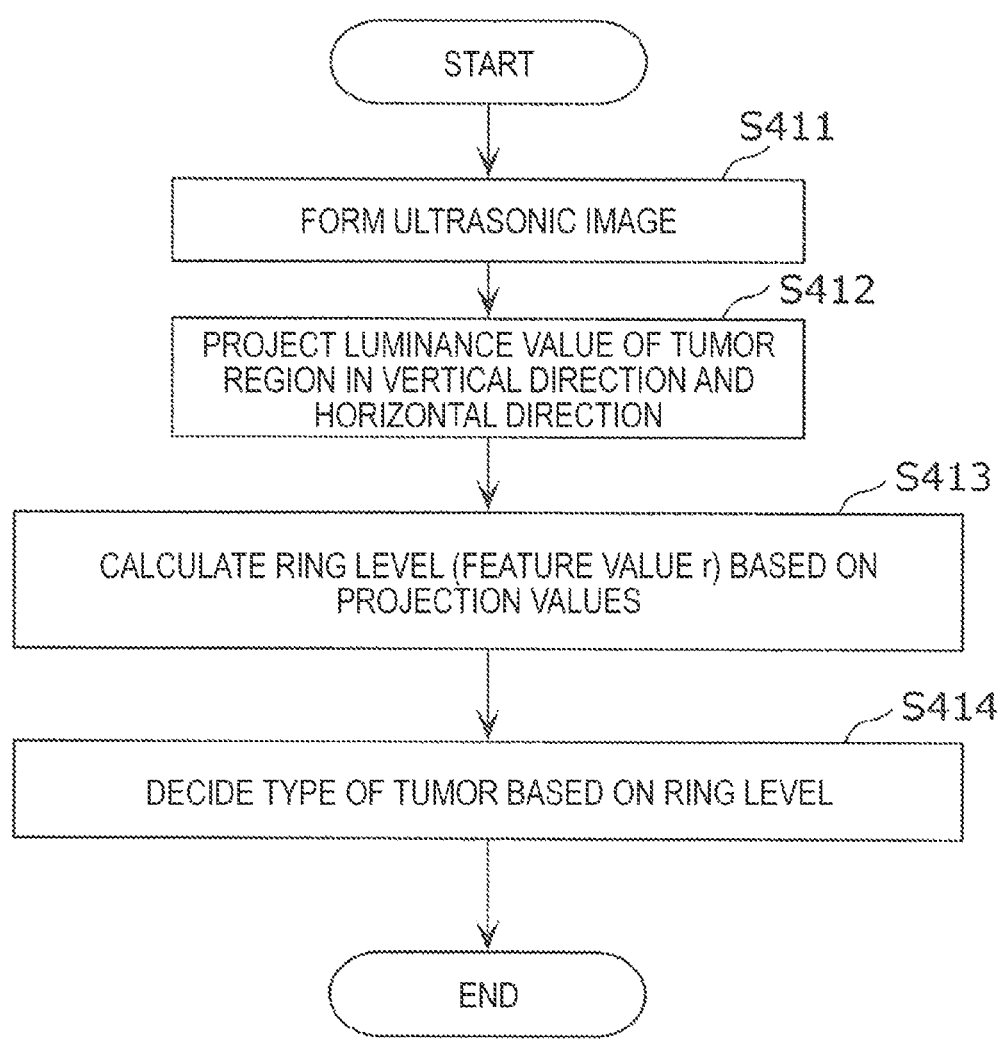
FIG. 24 is a flowchart showing operation executed by an ultrasonic diagnostic apparatus according to the third embodiment.

As discussed in the third embodiment, the ultrasonic diagnostic apparatus according to an aspect of the present invention executes a process shown in FIG. 24. Initially, the image forming unit 103 forms an ultrasonic image corresponding to echo signals received from a specimen after administration of a contrast medium (S411).

Then, the feature value calculating unit 106 projects a plurality of pixel luminance values contained in a tumor region including a tumor in the ultrasonic image such that the pixel luminance values are projected in the horizontal direction and the vertical direction (S412). Then, the feature value calculating unit 106 calculates a ring level (feature value r) indicating the degree of a ring shape based on the degrees of downward convexity exhibited in each of the projected results, as such a ring shape where the luminance value in the central portion becomes lower than the luminance value in the peripheral portion in the image of the tumor region (S413).

Then, the type deciding unit 107 decides the tumor type based on the ring level (S414).

Figure 25:
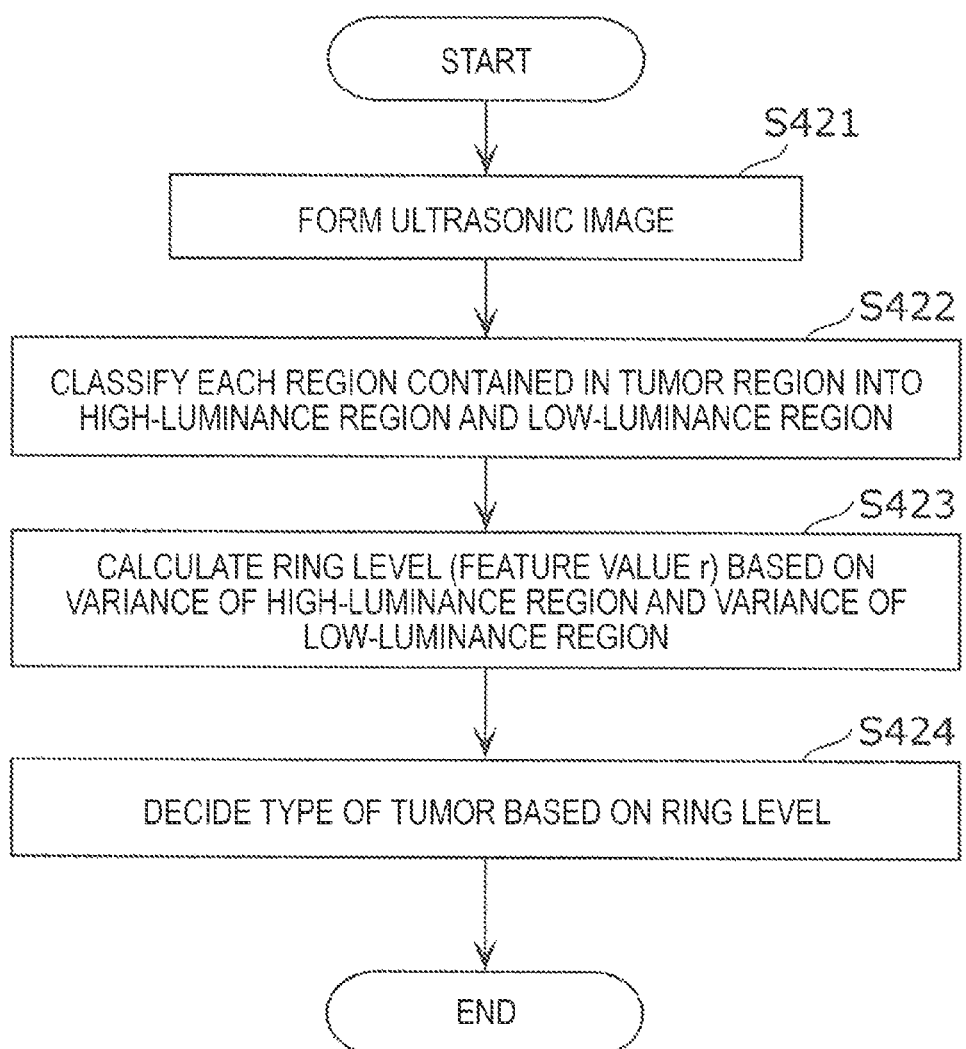
FIG. 25 is a flowchart showing operation executed by ultrasonic diagnostic apparatuses according to the fourth and fifth embodiment.

As discussed in the fourth embodiment and the fifth embodiment, the ultrasonic diagnostic apparatus according to an aspect of the present invention executes a process shown in FIG. 25. Initially, the image forming unit 103 forms an ultrasonic image corresponding to echo signals received from a specimen after administration of a contrast medium (S421).

Then, the feature value calculating unit 106 classifies each of a plurality of pixel regions contained in a tumor region including a tumor in the ultrasonic image into a low-luminance region, or a high-luminance region exhibiting higher luminance than in the low-luminance region (S422).

More specifically, as discussed in the fourth embodiment, the feature value calculating unit 106 classifies each of the plurality of regions contained in the tumor region into a low-luminance region when the luminance value of the region (such as average value) is smaller than a predetermined threshold, and classifies each of the regions into a high-luminance region when the luminance value of the region is larger than the predetermined threshold.

Alternatively, as discussed in the fifth embodiment, the feature value calculating unit 106 calculates a number sequence (TIC), which indicates a time-series change of the luminance value in the region, for each of the plurality of regions contained in the tumor region. Then, the feature value calculating unit 106 classifies each of the region into the low-luminance region when the difference between the maximum luminance value and the minimum luminance value in the number sequence is smaller than a predetermined threshold, and classifies each of the region into the high-luminance region when the difference between the maximum luminance value and the minimum luminance value in the number sequence is larger than the predetermined threshold.

The region in this context is a region containing at least one pixel.

Then, the feature value calculating unit 106 calculates a ring level (feature value r), which level indicates the degree of a ring shape where the luminance in the central portion becomes lower than the luminance value in the peripheral portion surrounding the central portion in the image of the tumor region, as a level calculated based on the difference between a variance at the position of the low-luminance region (variance at the position of at least one region classified into the low-luminance region) and a variance at the position of the high-luminance region (variance at the position of at least one region classified into the high-luminance region) (S423). More specifically, the feature value calculating unit 106 sets the ring level to a second value when the difference value obtained by subtracting the variance at the position of the low-luminance region from the variance at the position of the high-luminance region is a first value. On the other hand, the feature value calculating unit 106 sets the ring level to a fourth value larger than the second value when the difference value is a third value larger than the first value. In other words, the feature value calculating unit 106 sets a larger ring level when the difference value is large.

Then, the type deciding unit 107 decides the tumor type based on the ring level (S424).

The feature value calculating unit 106 may calculate the difference (feature value e) between the luminance of the tumor region and the luminance of a parenchyma region contained in the ultrasonic image and not including the tumor, and the type deciding unit 107 decides the tumor type based on the difference between the luminance of the tumor region and the luminance of the parenchyma region, and on the ring level.

Other Modified Examples

While exemplary embodiments according to the present invention have been described, it is obvious that the present invention is not limited to these embodiments. The following configurations are also included in the scope of the present invention.

(1) Specifically, each of the apparatuses described hereinabove is constituted by a computer system including a microprocessor, a ROM, a RAM, a hard disk unit, a display unit, a keyboard, a mouse and others. The RAM or the hard disk unit stores a computer program. The functions of each apparatus are performed in accordance with operation of the microprocessor under the computer program. The computer program in this context refers to a program constituted by a combination of a plurality of instruction codes indicating instructions issued to the computer to allow performance of predetermined functions.

(2) Apart or the whole of the constituent elements of each of the apparatuses may be constituted by a single system LSI (Large Scale Integration). The system LSI is a super multifunction LSI manufactured from a plurality of constituent units integrated on one chip. More specifically, the system LSI is a computer system including a microprocessor, a ROM, a RAM and others. The RAM stores a computer program. The functions of the system LSI are performed in accordance with operation of the microprocessor under the computer program.

(3) A part or the whole of the constituent elements of each of the apparatuses may be constituted by an IC card or a single module detachably attached to each of the apparatuses. The IC card or the module is a computer system constituted by a microprocessor, a ROM, a RAM and others. The IC card or the module may include the foregoing super multifunction LSI. The functions of the IC card or the module are performed in accordance with operation of the microprocessor under a computer program. The IC card or the module may have tamper resistance.

(4) The present invention may be practiced as a method for realizing the respective steps described herein. In addition, the present invention may be practiced in the form of a computer program executing these steps by the use of a computer, or in the form of digital signals under the computer program.

The present invention may be practiced in the form of a recording medium recording the computer program or the digital signals in a manner readable by a computer, such a recording medium as a flexible disk, a hard disk, a CD-ROM, an MO, a DVD, a DVD-ROM, a DVD-RAM, a BD (Blu-ray (registered trademark) Disc), and a semiconductor memory. In addition, the present invention may be practiced in the form of the digital signals recorded on any one of these recording media.

The present invention may be practiced in the form of the computer program or the digital signals transmitted via an electric communication line, a wireless or wired communication line, a network including the Internet as a typical example, data broadcasting or others.

The present invention may be practiced in the form of a computer system including a microprocessor and a memory. The memory stores the computer program, while the microprocessor operates under the computer program.

The present invention may be practiced by another independent computer system which receives the program or the digital signals transferred in the form of the recording medium recording the program or the digital signals, or transferred via the network.

(5) The respective embodiments and modified examples may be combined.

The respective constituent elements included in the respective embodiments may be constituted by dedicated hardware, or realized by execution of software programs appropriate for the respective constituent elements. The respective constituent elements may be realized by a program executing unit such as a CPU or a processor which reads and executes a software program recorded in a recording medium such as a hard disk and a semiconductor memory. In this case, the software realizing the ultrasonic diagnostic apparatuses and others according to the respective embodiments is the following program.

The program is a program for causing a computer executes an ultrasonic diagnostic method that decides a type of a tumor contained in a specimen, and includes: an image forming step that forms an ultrasonic image corresponding to an echo signal received from the specimen after administration of a contrast medium; a feature value calculating step that classifies each of a plurality of pixel regions contained in a tumor region including the tumor in the ultrasonic image into a low-luminance region, or a high-luminance region having higher luminance than the luminance of the low-luminance region, and calculates, based on a difference between a variance at a position of the low-luminance region and a variance at a position of the high-luminance region, a ring level indicating a degree of a ring shape of an image of the tumor region, the ring shape in which a luminance value of a central portion is lower than a luminance value of a peripheral portion surrounding the central portion; and a type deciding step that decides the type of the tumor based on the ring level.

A program according to an aspect of the present invention is a program for causing a computer to execute an ultrasonic diagnostic method that decides a type of a tumor contained in a specimen, and includes: an image forming step that forms an ultrasonic image corresponding to an echo signal received from the specimen after administration of a contrast medium; a region of interest setting step that searches for a first region of interest corresponding to a central portion in a ring shape in a tumor region containing the tumor in the ultrasonic image, the ring shape in which a luminance value of the central portion is lower than a luminance value of a peripheral portion surrounding the central portion; a feature value calculating step that calculates a difference between luminance of the first region of interest and luminance of a second region of interest corresponding to the peripheral portion to designate the difference as a ring level indicating a degree of the ring shape of an image of the tumor region; and a type deciding step that decides the type of the tumor based on the ring level.

A program according to an aspect of the present invention is a program for causing a computer to execute an ultrasonic diagnostic method that decides a type of a tumor contained in a specimen, and includes: an image forming step that forms an ultrasonic image corresponding to an echo signal received from the specimen after administration of a contrast medium; a feature value calculating step that projects luminance values of a plurality of pixels contained in a tumor region including the tumor in the ultrasonic image such that the luminance values are projected in a horizontal direction and a vertical direction, and calculates, based on degrees of downward convexity exhibited in the projected results, a ring level indicating a degree of a ring shape of an image of the tumor region, the ring shape in which a luminance value of the central portion is lower than a luminance value of a peripheral portion surrounding the central portion, the ring level calculated; and a type deciding step that decides the type of the tumor based on the ring level.

The numerals shown in the above description are all presented only for describing specific examples of the present invention, and not for limiting the scope of the present invention.

Division of function blocks illustrated in the block diagrams is presented by way of example only. A single function block may be provided in place of a plurality of function blocks, or a single function block may be divided into a plurality of blocks. Moreover, a part of functions of certain function block or blocks may be shifted to different function block or blocks. In addition, functions of a plurality of function blocks having similar functions may be processed in parallel or in a time-sharing manner by single hardware or software.

The order of execution of a plurality of steps included in the ultrasonic diagnostic method performed by the ultrasonic diagnostic apparatus is presented only for describing a specific example of the present invention, and therefore may be an order different from the order described herein. In addition, a part of the steps may be executed simultaneously (in parallel) with other steps.

While the ultrasonic diagnostic apparatus according to one or a plurality of aspects of the present invention has been described based on exemplary embodiments, the present invention is not limited to these exemplary embodiments. Modes containing various modifications which may be made by those skilled in the art, and modes constituted by combinations of constituent elements in different embodiments may be included in the scope of one or a plurality of aspects of the present invention without departing from the scope of the present invention.

INDUSTRIAL APPLICABILITY

The present invention is applicable to an ultrasonic diagnostic apparatus. The present invention is also applicable to an ultrasonic diagnostic method.

REFERENCE SIGNS LIST 60 section of interest
61 feature value
70 tumor region
71 hypoechogenic region
72 differential filter
73 coefficient of periphery
74 coefficient of center
75 search region
80 predetermined pattern
81 input pattern
91 small region
92, 94 high-luminance region
93, 95 low-luminance region
100 ultrasonic diagnostic apparatus
101 ultrasonic probe
102 ultrasonic wave transmitting and receiving unit
103 image forming unit
104 data storing unit
105 region of interest setting unit
106 feature value calculating unit
107 type deciding unit
108 display screen creating unit
109 input value acquiring unit
110 input device
111 display device
G10, G20 display screen
G11 ultrasonic image
G12, G23A, G23B tumor region
G13, G24A, G24B parenchyma region
G21 contrast image
G22 tissue image
G25 feature value transition

The invention claimed is:

1. An ultrasonic diagnostic apparatus that decides a type of a tumor contained in a specimen, the apparatus comprising:
   an image forming unit that forms an ultrasonic image corresponding to an echo signal received from the specimen after administration of a contrast medium;
   a feature value calculating unit that classifies each of a plurality of pixel regions contained in a tumor region including the tumor in the ultrasonic image into a low-luminance region, or a high-luminance region having higher luminance than the luminance of the low-luminance region, and calculates, based on a difference between a variance at a position of the low-luminance region and a variance at a position of the high-luminance region, a ring level indicating a degree of a ring shape of an image of the tumor region, the ring shape in which a luminance value of a central portion is lower than a luminance value of a peripheral portion surrounding the central portion; and a type deciding unit that decides the type of the tumor based on the ring level.

2. The ultrasonic diagnostic apparatus according to claim 1, wherein the feature value calculating unit sets the ring level to a second value when a difference value obtained by subtracting the variance at the position of the low-luminance region from the variance at the position of the high-luminance region is a first value, and sets the ring level to a fourth value larger than the second value when the difference value is a third value larger than the first value.

3. The ultrasonic diagnostic apparatus according to claim 1, wherein the feature value calculating unit classifies each of the regions into the low-luminance region when the luminance value of the region is smaller than a predetermined threshold, and classifies each of the regions into the high-luminance region when the luminance value of the region is larger than the threshold.

4. The ultrasonic diagnostic apparatus according to claim 1, wherein the feature value calculating unit calculates a number sequence indicating a time-series change of the luminance value for each of the regions, classifies each of the regions into the low-luminance region when a difference between the maximum luminance value and the minimum luminance value in the number sequence is smaller than a predetermined threshold, and classifies each of the pixels into the high-luminance region when the difference is larger than the threshold.

5. The ultrasonic diagnostic apparatus according to claim 1, wherein the feature value calculating unit further calculates a difference between luminance of a parenchyma region contained in the ultrasonic image and not including the tumor, and luminance of the tumor region, and the type deciding unit decides the type of the tumor based on the difference between the luminance of the parenchyma region and the luminance of the tumor region, and on the ring level.

6. An ultrasonic diagnostic method that decides a type of a tumor contained in a specimen, the method comprising:

an image forming step that forms an ultrasonic image corresponding to an echo signal received from the specimen after administration of a contrast medium;

a feature value calculating step that classifies each of a plurality of pixel regions contained in a tumor region including the tumor in the ultrasonic image into a low-luminance region, or a high-luminance region having higher luminance than the luminance of the low-luminance region, and calculates, based on a difference between a variance at a position of the low-luminance region and a variance at a position of the high-luminance region, a ring level indicating a degree of a ring shape of an image of the tumor region, the ring shape in which a luminance value of a central portion is lower than a luminance value of a peripheral portion surrounding the central portion; and a type deciding step that decides the type of the tumor based on the ring level.

7. A program stored on a non-transitory medium for causing a computer to execute the ultrasonic diagnostic method according to claim 6.

* * * * *